(12) United States Patent
Longo

(10) Patent No.: US 7,070,217 B2
(45) Date of Patent: Jul. 4, 2006

(54) COLLISION ENERGY-ABSORBING DEVICE

(75) Inventor: Thomas W. Longo, Sterling Heights, MI (US)

(73) Assignee: Magna International Inc., Ontario (CA)

( * ) Notice: Subject to any disclaimer, the term of this patent is extended or adjusted under 35 U.S.C. 154(b) by 0 days.

(21) Appl. No.: 10/511,752

(22) PCT Filed: Apr. 17, 2003

(86) PCT No.: PCT/US03/11908

§ 371 (c)(1),
(2), (4) Date: Oct. 19, 2004

(87) PCT Pub. No.: WO03/089805

PCT Pub. Date: Oct. 30, 2003

(65) Prior Publication Data

US 2005/0253403 A1 Nov. 17, 2005

Related U.S. Application Data

(60) Provisional application No. 60/373,607, filed on Apr. 19, 2002.

(51) Int. Cl.
*B60R 19/26* (2006.01)

(52) U.S. Cl. ...................................... 293/132; 293/133

(58) Field of Classification Search ................ 293/132, 293/133, 155; 188/376, 377
See application file for complete search history.

(56) References Cited

U.S. PATENT DOCUMENTS

| | | | |
|---|---|---|---|
| 3,146,014 A * | 8/1964 | Kroell ........................ 293/133 |
| 3,479,902 A | 11/1969 | Okamoto | |
| 4,023,652 A * | 5/1977 | Torke ......................... 293/133 |
| 5,224,574 A * | 7/1993 | Thum ......................... 188/377 |
| 5,293,973 A * | 3/1994 | Thum ......................... 293/133 |
| 5,314,229 A * | 5/1994 | Matuzawa et al. .......... 293/133 |
| 5,404,974 A * | 4/1995 | Thum et al. ................ 293/122 |
| 5,549,327 A * | 8/1996 | Rusche et al. .............. 280/751 |
| 5,597,055 A * | 1/1997 | Han et al. ................... 188/371 |
| 6,062,355 A * | 5/2000 | Nohr et al. ................. 188/371 |
| 6,189,941 B1 * | 2/2001 | Nohr ........................... 293/119 |
| 6,282,769 B1 * | 9/2001 | Longo et al. ................ 29/417 |
| 6,293,587 B1 * | 9/2001 | Lapic et al. ................ 293/133 |
| 6,386,347 B1 * | 5/2002 | Reynaert .................... 188/377 |
| 6,409,239 B1 * | 6/2002 | Tjoelker et al. ............ 293/132 |
| 6,422,604 B1 * | 7/2002 | Lapic .......................... 293/133 |
| 6,554,333 B1 * | 4/2003 | Shimotsu et al. ........... 293/132 |

(Continued)

FOREIGN PATENT DOCUMENTS

DE  24 27 764  1/1976

(Continued)

*Primary Examiner*—Kiran B. Patel
(74) *Attorney, Agent, or Firm*—Pillsbury Winthrop Shaw Pittman, LLP

(57) ABSTRACT

A collision energy-absorbing device includes a body member connected between the frame assembly of a motor vehicle and a bumper beam. The body member collapses as the bumper beam and the frame assembly are moved relatively toward one another during a vehicle collision. The body member has a first telescoping portion and a second telescoping portion that are connected by a connecting portion. The telescoping portions have different cross-sectional dimensions to enable the telescoping portions to move one within the other into collapsing telescoping relation as the body member collapses with the connecting portion being deformed and received between the telescoping portions. One or more protrusions extending from one of the telescoping portions interfere with relative movement of the other of the telescoping portions to retard movement of the telescoping portions into telescoping relation.

1 Claim, 20 Drawing Sheets

U.S. PATENT DOCUMENTS

| | | | |
|---|---|---|---|
| 6,681,907 B1* | 1/2004 | Le | 293/133 |
| 6,702,345 B1* | 3/2004 | Yoshida | 293/133 |
| 6,802,548 B1* | 10/2004 | Shimotsu | 293/133 |
| 6,854,574 B1* | 2/2005 | Yoshida et al. | 293/133 |
| 6,905,136 B1* | 6/2005 | Vidal et al. | 280/752 |
| 6,908,129 B1* | 6/2005 | Shimotsu | 293/132 |
| 6,942,262 B1* | 9/2005 | Glasgow et al. | 293/132 |
| 2001/0022444 A1 | 9/2001 | Lapic | |
| 2003/0209915 A1* | 11/2003 | Yoshida | 293/133 |
| 2005/0110240 A1* | 5/2005 | Dornbos | 280/495 |

FOREIGN PATENT DOCUMENTS

| | | |
|---|---|---|
| DE | 42 40 237 A1 | 6/1994 |
| DE | 100 02 379 A1 | 8/2001 |
| EP | 0 717 215 B1 | 6/1996 |
| FR | 2 730 025 | 8/1996 |
| JP | 02175452 | 7/1990 |

* cited by examiner

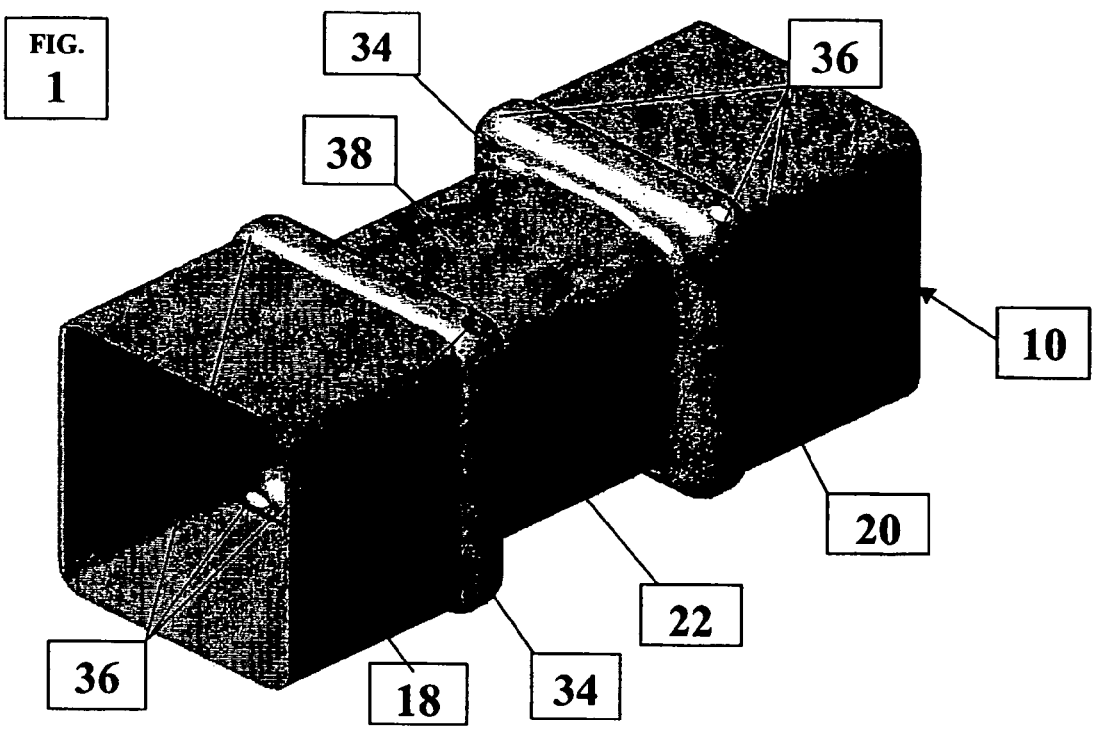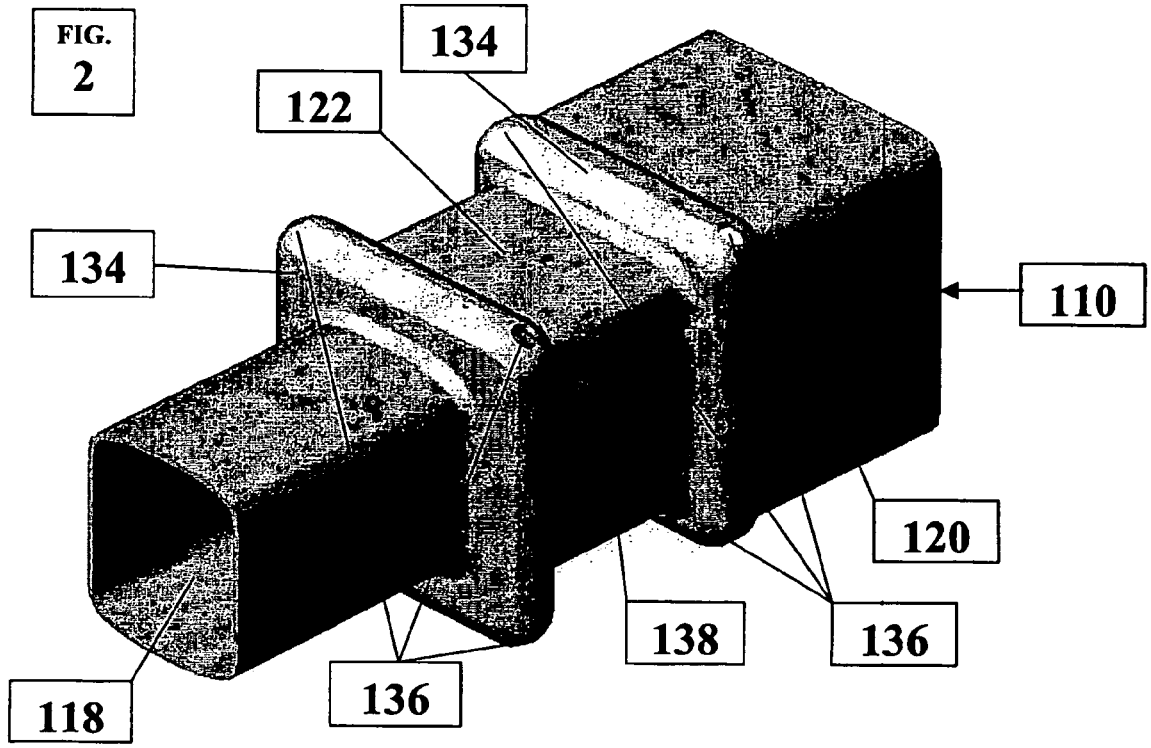

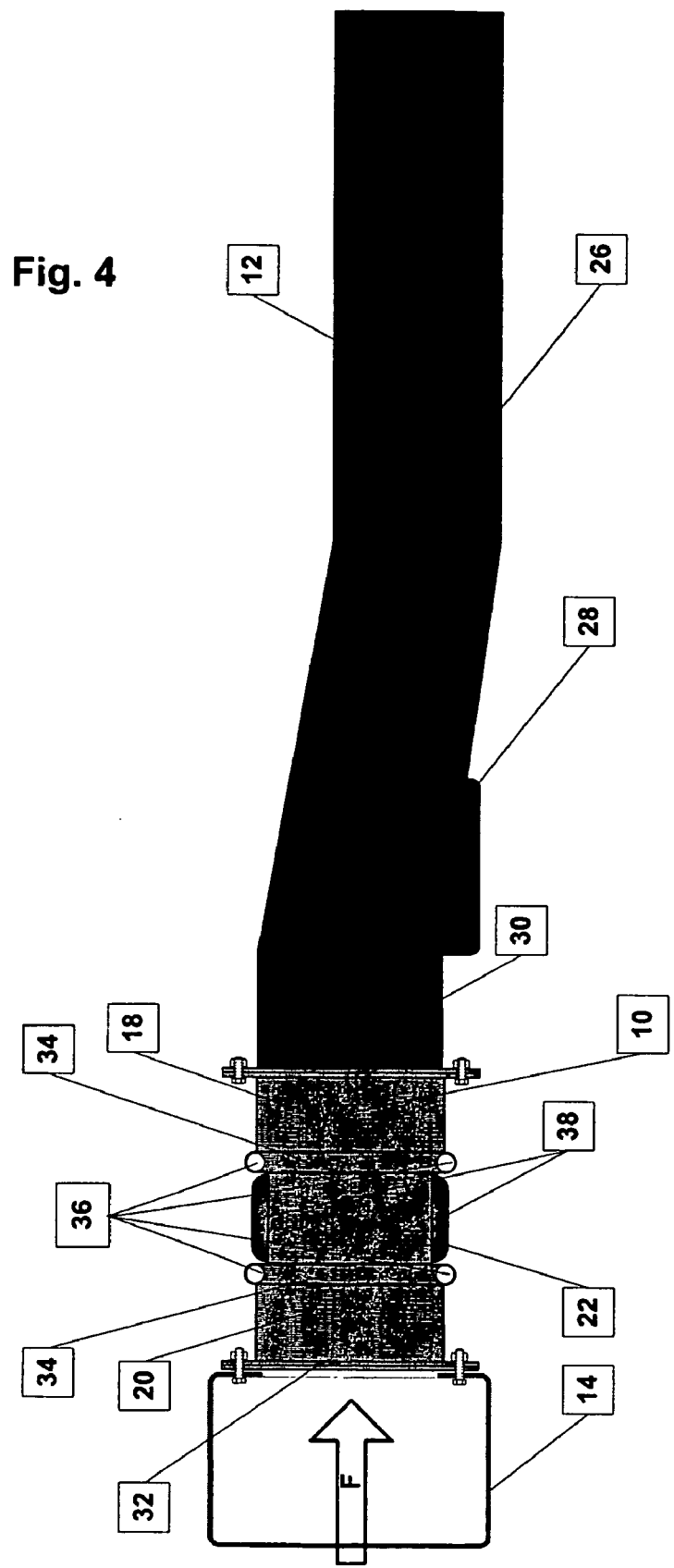

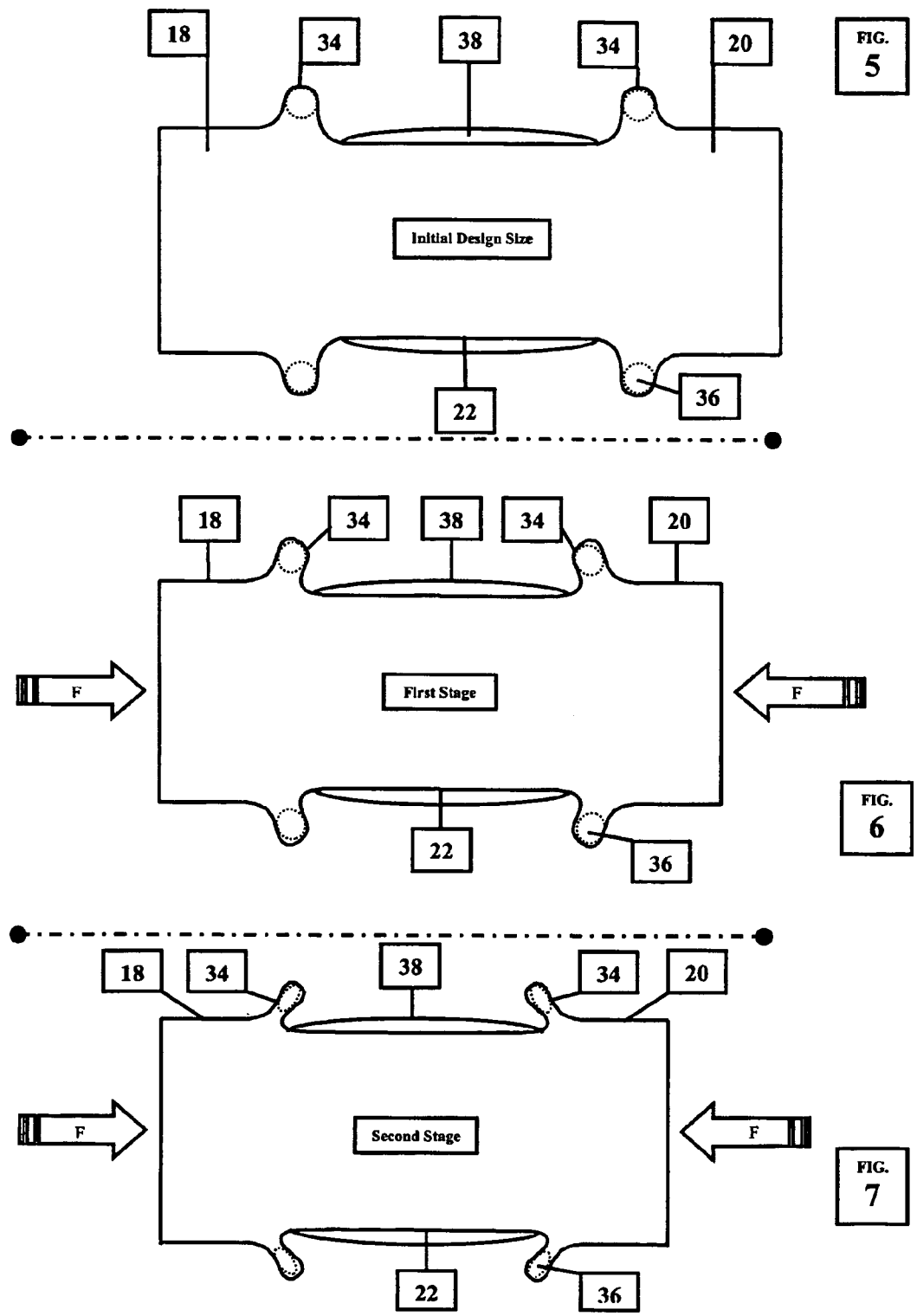

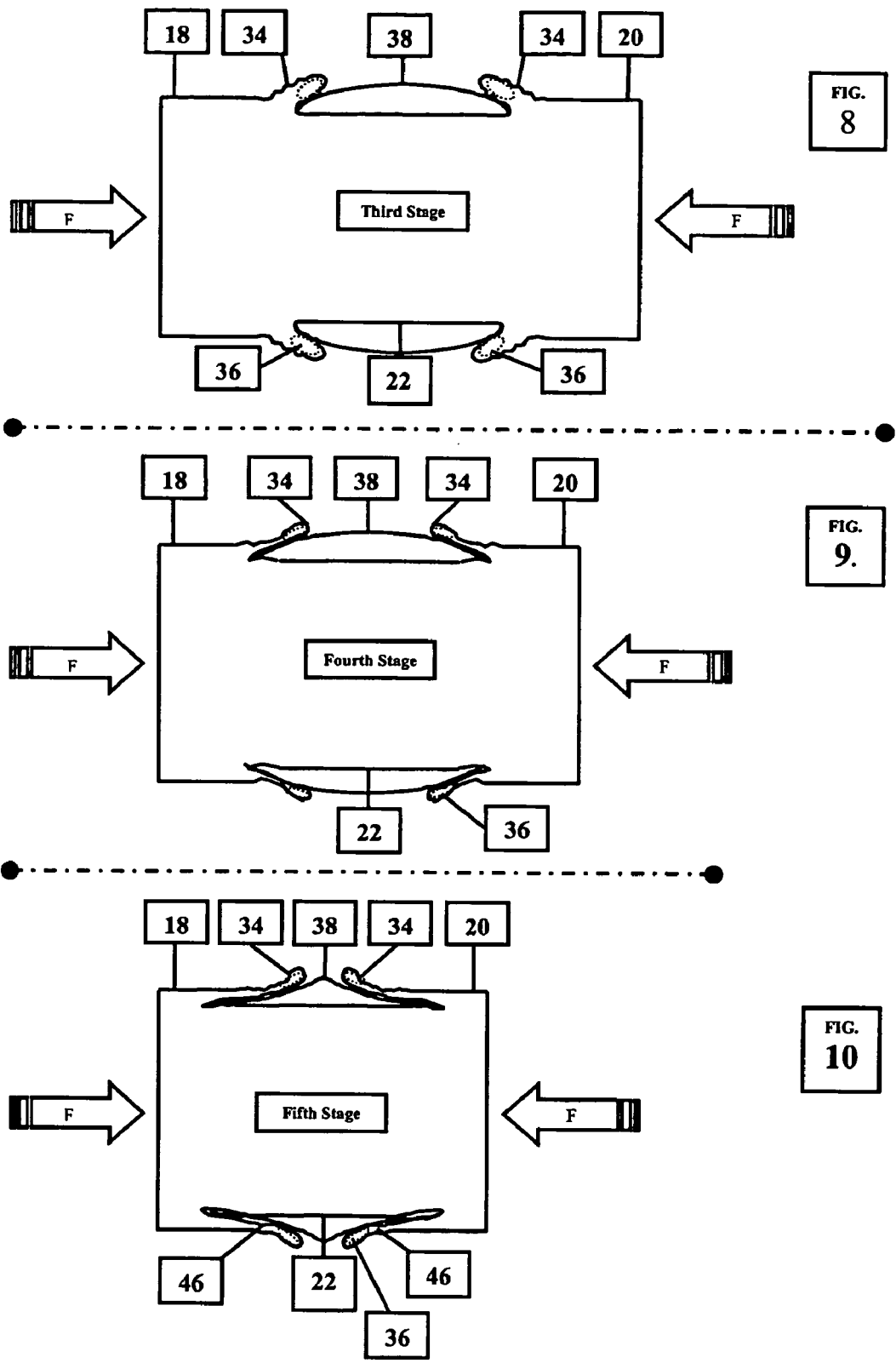

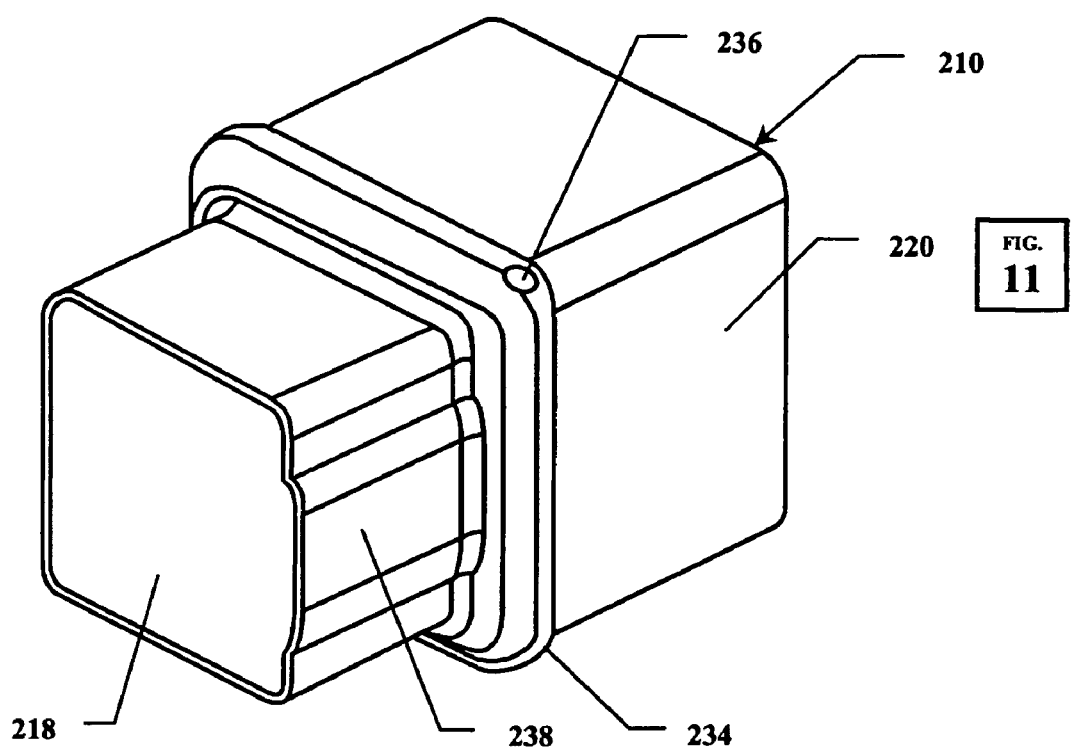
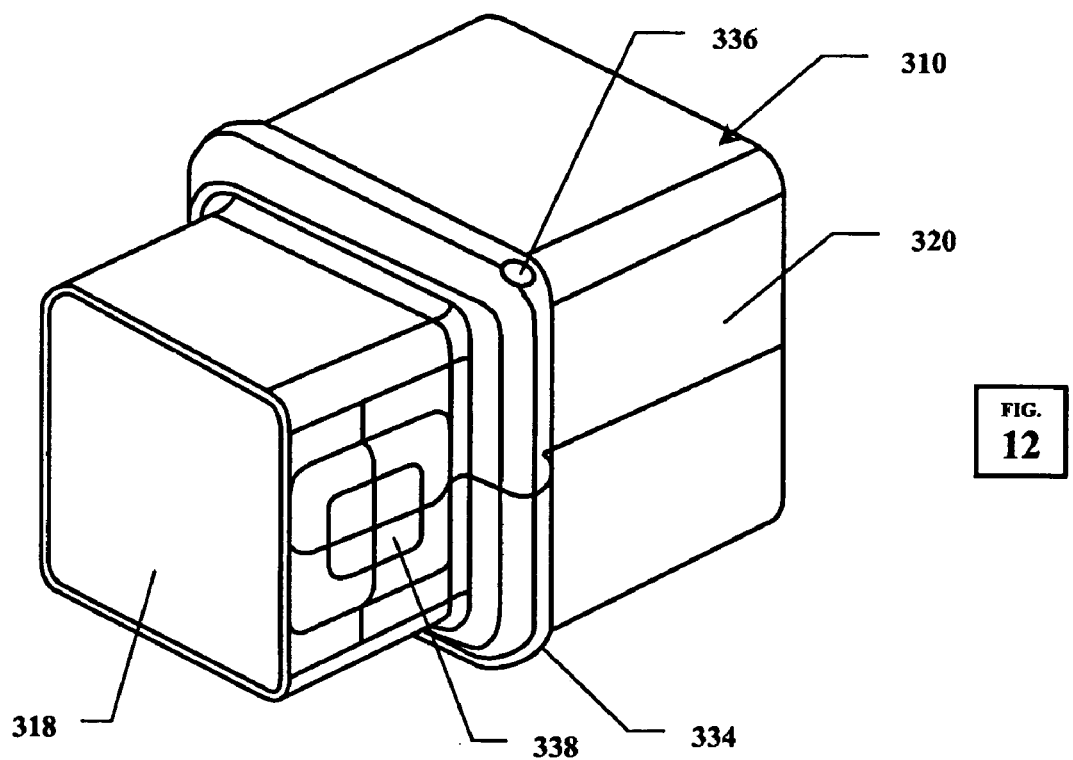

Section View
of attachment to
Bumper Beam

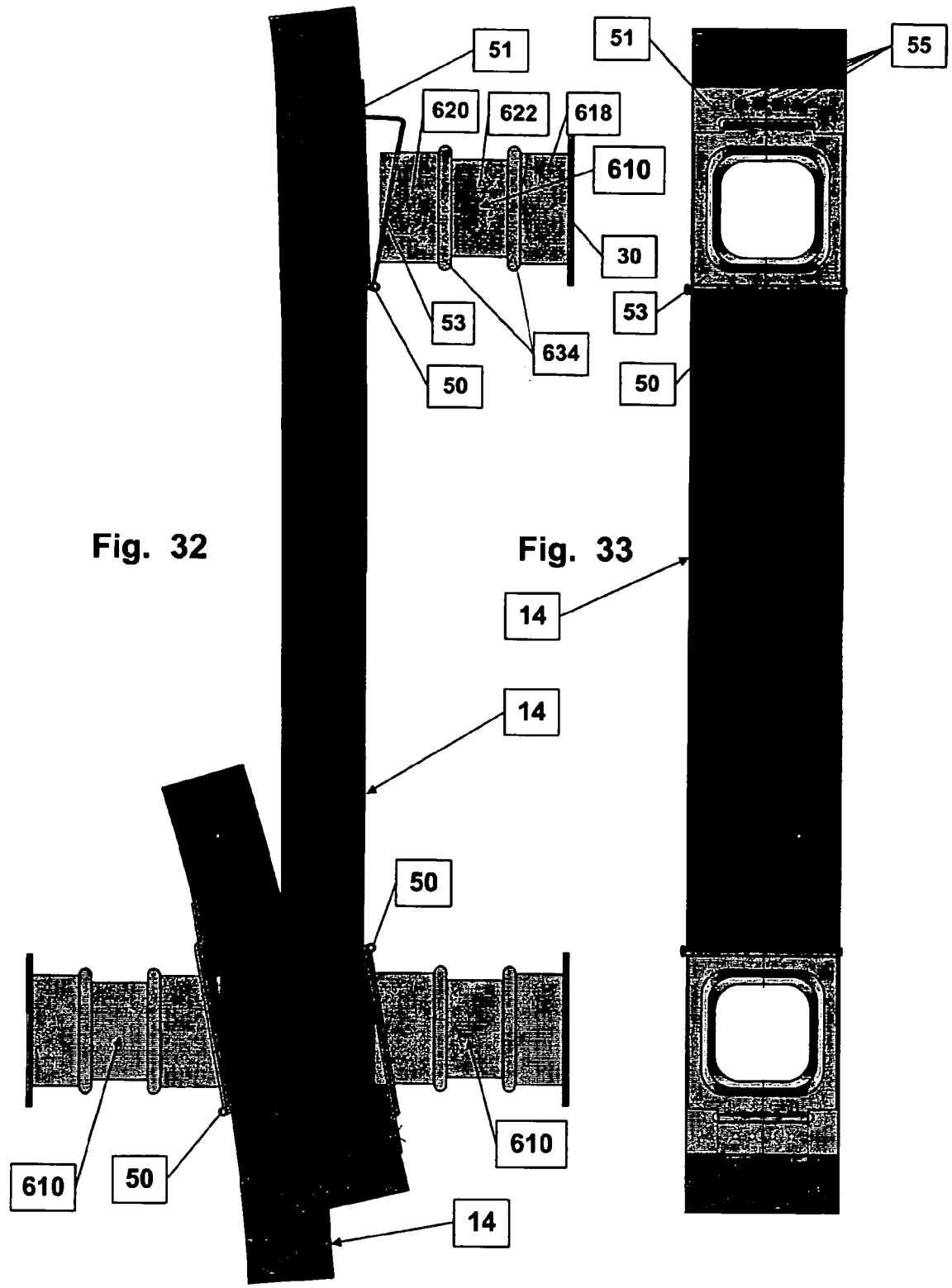

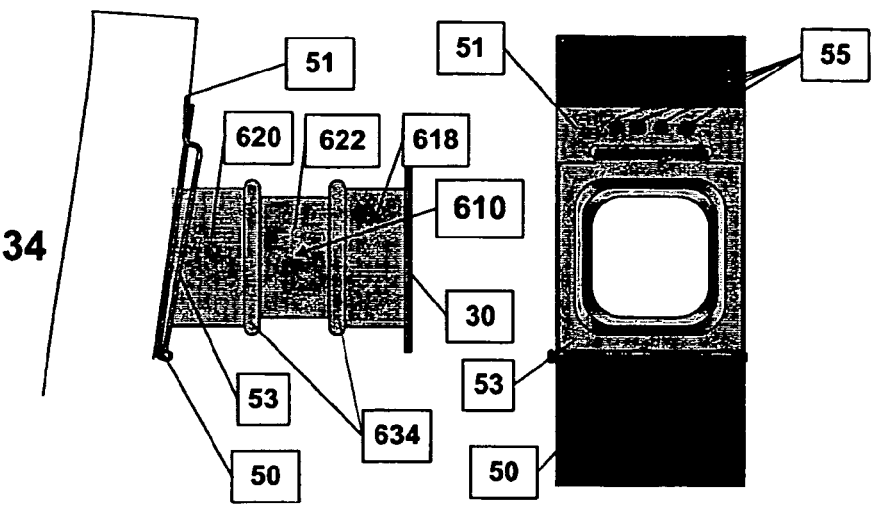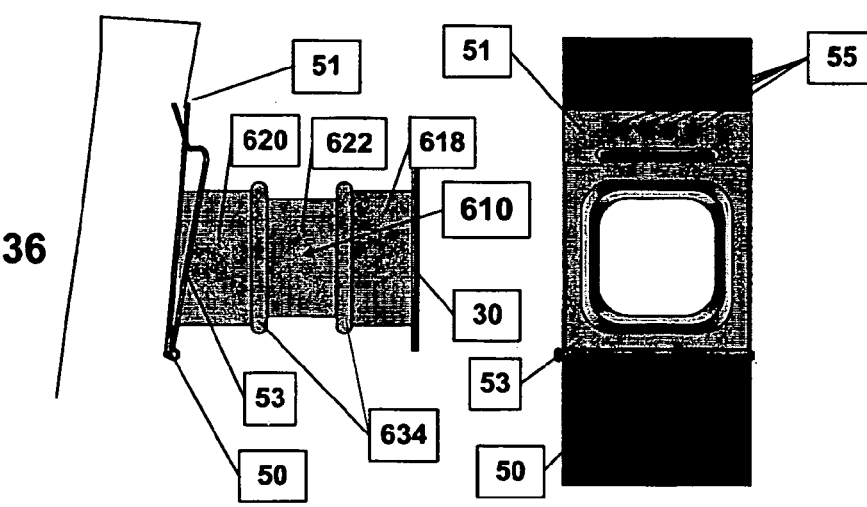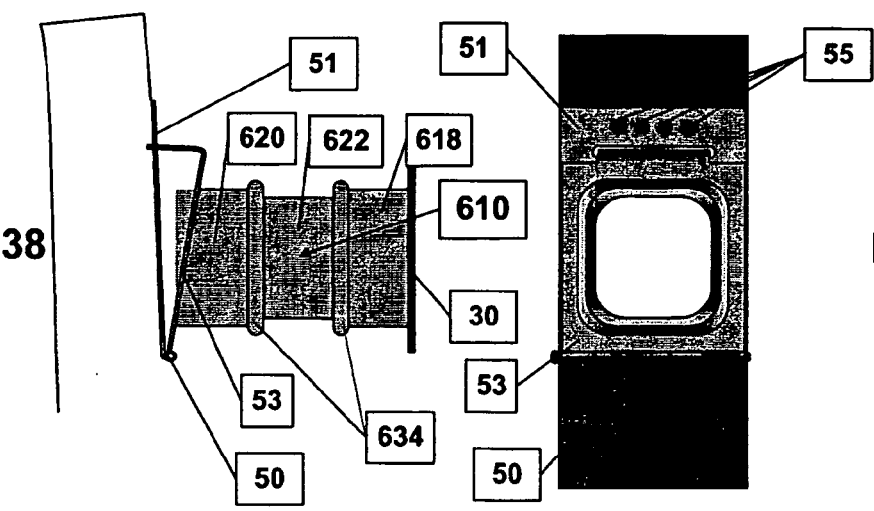

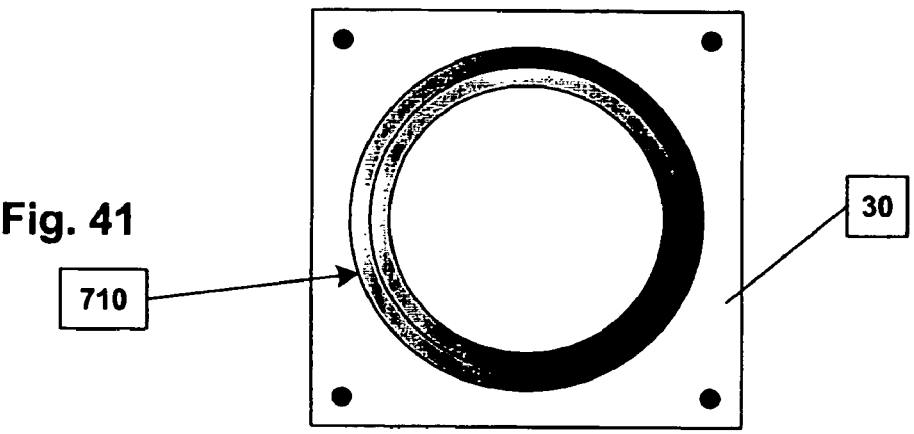
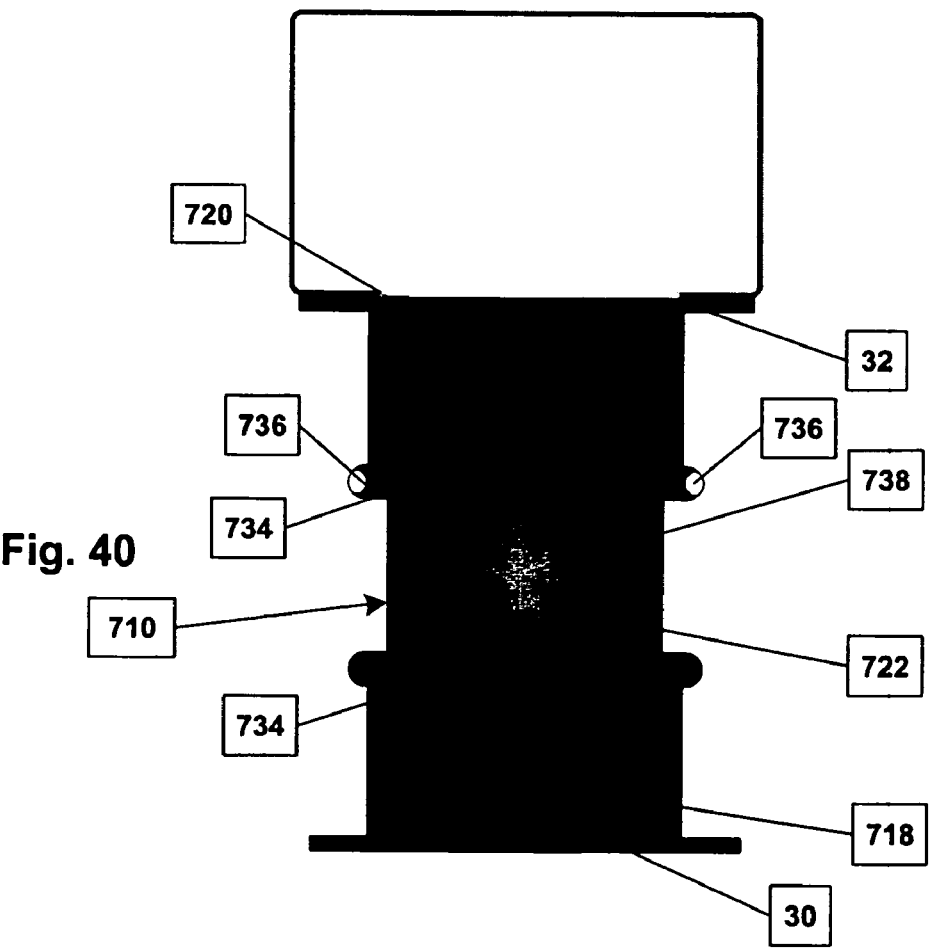

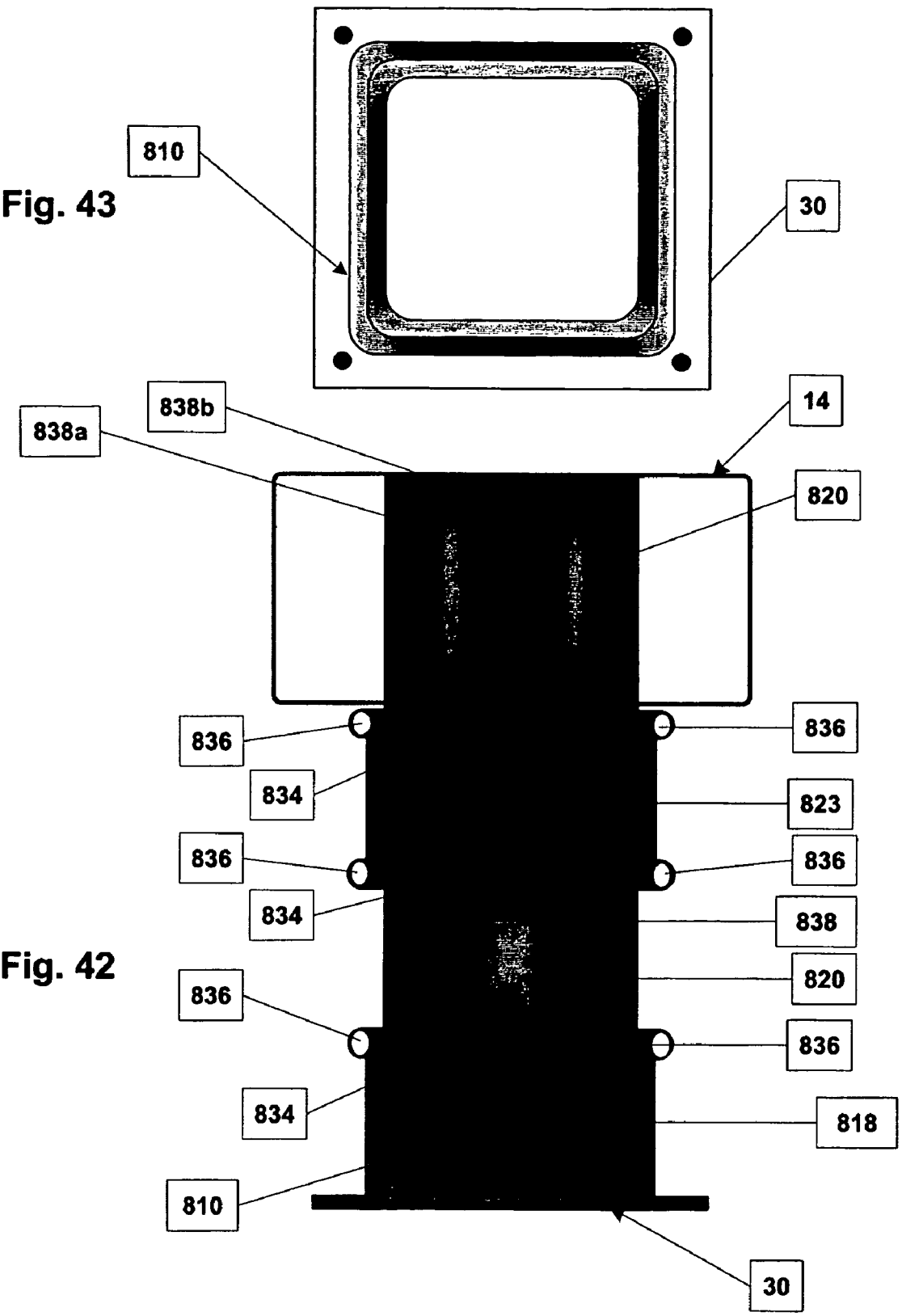

COLLISION ENERGY-ABSORBING DEVICE

CROSS REFERENCE TO RELATED APPLICATION

This is the U.S. National Stage of PCT/US03/011908, filed Apr. 17, 2003, which in turn claims priority to U.S. Provisional Patent Application No. 60/373,607, filed Apr. 19, 2002, both of which are incorporated herein in their entirety by reference.

FIELD OF THE INVENTION

The present invention relates to a collision energy-absorbing device for mounting between a frame of a motor vehicle and a bumper beam at one end of the motor vehicle.

BACKGROUND OF THE INVENTION

In conventional vehicle frame assemblies, bumper beams are fixedly mounted to frame rails at the front and rear ends of the vehicle. During a front or rear end collision in the longitudinal direction of the vehicle, the collision forces are received by the bumper beam and transmitted to the frame assembly via the connection between the bumper beam and the frame rails. In situations involving relatively high collision forces, transferring the collision energy directly to the vehicle frame assembly without some type of cushioning or dissipation can deform the frame rails or otherwise damage the frame assembly. Repairing damaged vehicle frame assemblies after a collision can be quite expensive.

To solve this problem, it has been known to intentionally weaken end portions of the frame rails so that the weakened end portions collapse during collision and dissipate some or all of the collision energy, thereby reducing the amount of collision energy transmitted to the remainder of the frame and the passenger compartment. These weakened end portions are referred to as "crush zones." Providing these crush zones in the vehicle frame assembly adds significant complexity and increases the overall cost of manufacturing the vehicle frame assembly. Another problem with these crush zones is that they often tend to buckle and fold outwardly rather than collapsing only in the direction of the impact force (i.e. the longitudinal direction of the vehicle). This requires that there be sufficient room to accommodate such outward folding and ensure the proper energy dissipation.

As an alternative, it has been known to provide tubular crush zones that collapse in an accordion-like manner. An example of such an arrangement is disclosed in PCT Application WO 98/39106. The problem with this type of arrangement is that it is difficult to achieve satisfactory energy dissipation using only a pair of these accordion-type crush zones. Specifically, the amount of deformation allowed in these accordion-type crush zones is limited by its width. That is, once the accordion folds contact the opposing wall, there will be no further deformation of the crush zone and the remaining collision forces will be transmitted to the frame assembly undissipated.

Consequently, it would be desirable to provide a more effective alternative for providing crush zones to dissipate the collision energy during a front or rear end collision and thereby reduce the amount of energy being transferred to the vehicle frame assembly.

Further, in a frontal offset collision, impact occurs at one end of the bumper beam. During impact, the opposite end of the bumper beam pivots and tends to pivot the vehicle due to the rigid connection with the vehicle frame assembly. Specifically, as the end of the bumper beam which has been impacted is forced in towards the frame assembly, the opposite end swings in a direction away from the frame assembly. This tends to pull on that side of the frame assembly and pivot the vehicle in a yaw-type movement. Consequently, it would be desirable to prevent this pivoting movement of the vehicle during a frontal offset collision.

SUMMARY OF THE INVENTION

The disadvantages of the prior art may be overcome by providing a collision energy-absorbing device (CEAD) for mounting between a frame assembly of a motor vehicle and a bumper beam at one end of the motor vehicle. The collision energy-absorbing device includes a substantially tubular body member configured to be operatively connected between the vehicle frame assembly and the bumper beam. The body member is constructed and arranged to collapse as the bumper beam and the vehicle frame assembly are moved relatively toward one another during a vehicle collision, such as a head-on collision or an offset crash. The body member has a substantially tubular first telescoping portion and a substantially tubular second telescoping portion connected by a connecting portion. The first and second telescoping portions have different cross-sectional dimensions configured to enable the first and second telescoping portions to move one within the other into collapsing telescoping relation as the body member collapses with the connecting portion being deformed and received between the first and second telescoping portions. The body member further includes one or more protrusions extending from one of the first and second telescoping portions. The protrusions are configured to interfere with relative movement of the other of the first and second telescoping portions as the body member collapses to thereby retard movement of the first and second telescoping portions one within the other into the telescoping relation.

In accordance with still another aspect of the present invention, there is provided the combination including a motor vehicle having a frame assembly and a collision energy-absorbing system. The energy-absorbing system includes a collision energy-absorbing device and a bumper beam. The energy-absorbing device includes a substantially tubular body member configured to be operatively connected between the vehicle frame assembly and the bumper beam. The body member is constructed and arranged to collapse as the bumper beam and the vehicle frame assembly are moved relatively toward one another during a vehicle collision. The body member of the energy-absorbing device has a substantially tubular first telescoping portion and a substantially tubular second telescoping portion connected by a connecting portion. The first and second telescoping portions have different cross-sectional dimensions configured to enable the first and second telescoping portions to move one within the other into collapsing telescoping relation as the body member collapses with the connecting portion being deformed and received between the first and second telescoping portions. The body member further includes one or more protrusions extending from one of the first and second telescoping portions. The protrusions are configured to interfere with relative movement of the other of the first and second telescoping portions as the body member collapses to thereby retard movement of the first and second telescoping portions one within the other into the telescoping relation.

In accordance with still another aspect of the present invention, there is provided a collision energy-absorbing device for mounting between a frame assembly of a motor vehicle and a bumper beam at one end of the motor vehicle. The energy-absorbing device includes a substantially tubular body member configured to be operatively connected between the vehicle frame assembly and the bumper beam. The body member is constructed and arranged to collapse as the bumper beam and the vehicle frame assembly are moved relatively toward one another during a vehicle collision. The body member has a substantially tubular first telescoping portion and a substantially tubular second telescoping portion connected by a connecting portion. The first and second telescoping portions have different cross-sectional dimensions configured to enable the first and second telescoping portions to move one within the other into collapsing telescoping relation as the body member collapses with the connecting portion being deformed and received between the first and second telescoping portions. The body member further includes one or more perforations formed through the connecting portion to thereby weaken the connecting portion.

In accordance with still another aspect of the present invention, there is provided the combination including: a motor vehicle having a frame assembly, a pair of lost motion connecting structures each having a first mounting portion and a second mounting portion movably mounted to one another, the second mounting portions being connected to spaced lateral portions of the vehicle frame assembly; and a bumper beam operatively connected to the first mounting portions of the lost motion connecting structures. The lost motion connecting structures are constructed and arranged such that during an offset collision proximate one of the lost motion connecting structures the first mounting portion of the other lost motion connecting structure moves relative to the second mounting portion to permit the portion of the bumper associated therewith to move relatively away from the frame assembly.

In accordance with still another aspect of the present invention, there is provided a pair of lost motion connecting structures for mounting between spaced lateral portions of a frame assembly of a motor vehicle and a bumper beam at one end of the motor vehicle. Each lost motion connecting structure includes a first mounting portion and a second mounting portion movably mounted to one another. The first mounting portions are operatively connected to the bumper beam and the second mounting portions are operatively connected to the spaced lateral portions of the vehicle frame assembly. The lost motion connecting structures are constructed and arranged such that during an offset collision proximate one of the lost motion connecting structures the first mounting portion of the other lost motion connecting structure moves relative to the second mounting portion to permit the portion of the bumper associated therewith to move relatively away from the frame assembly.

Other objects, features, and advantages of this invention will become apparent from the following detailed description when taken in conjunction with the accompanying drawings, which are a part of this disclosure and which illustrate, by way of example, the principles of this invention.

BRIEF DESCRIPTION OF THE DRAWINGS

The accompanying drawings facilitate an understanding of the various embodiments of this invention. In such drawings:

FIG. 1 is a perspective view of an embodiment of a collision energy-absorbing device constructed according to the principles of the present invention;

FIG. 2 is a perspective view of another embodiment of a collision energy-absorbing device constructed according to the principles of the present invention;

FIG. 4 is a side view illustrating the absorbing device of FIG. 1 mounted between a frame of a motor vehicle and a bumper at one end of the motor vehicle;

FIG. 5 is a longitudinal section view of the absorbing device shown in FIG. 1 in its normal, uncollapsed condition;

FIG. 6 is a longitudinal section view of the absorbing device shown in FIG. 1 as an initial collision force is applied thereto;

FIG. 7 is a longitudinal section view of the absorbing device shown in FIG. 1 at the onset of telescoping;

FIG. 8 is a longitudinal section view of the absorbing device shown in FIG. 1 at a later stage of telescoping;

FIG. 9 is a longitudinal section view of the absorbing device shown in FIG. 1 in the final stages of collapse;

FIG. 10 is a longitudinal section view of the absorbing device shown in FIG. 1 in the fully collapsed condition;

FIGS. 11–14 are perspective views of other embodiments of the present invention;

FIG. 32 is a plan view of an offset impact to show how the opposite side in an impact will hinge;

FIG. 33 is a rear view of the offset impact shown in FIG. 32;

FIG. 34 is a plan view of an energy-absorbing system with first and second plate members beginning to pivot relative to one another;

FIG. 35 is a rear view of the energy-absorbing system shown in FIG. 34;

FIG. 36 is a plan view of an energy-absorbing system at a later stage of pivotal movement between first and second plate members;

FIG. 37 is a rear view of the energy-absorbing system shown in FIG. 36;

FIG. 38 is a plan view of an energy-absorbing system with the first and second plate members in an substantially open position;

FIG. 39 is a rear view of the energy-absorbing system shown in FIG. 38;

FIG. 40 is a plan view of a round collision energy-absorbing device having a 2-stage design with protrusions and perforations and being mounted to a bumper beam;

FIG. 41 is a rear view of the collision energy-absorbing device shown in FIG. 40;

FIG. 42 is a plan view of a square or rectangular collision energy-absorbing device having a 3-stage design with protrusions and perforations and being attached to the bumper face that allows absorption during the initial vehicle impact;

FIG. 43 is a rear view of the collision energy-absorbing device shown in FIG. 42;

DETAILED DESCRIPTION OF PREFERRED EMBODIMENTS OF THE INVENTION

Figure 3:
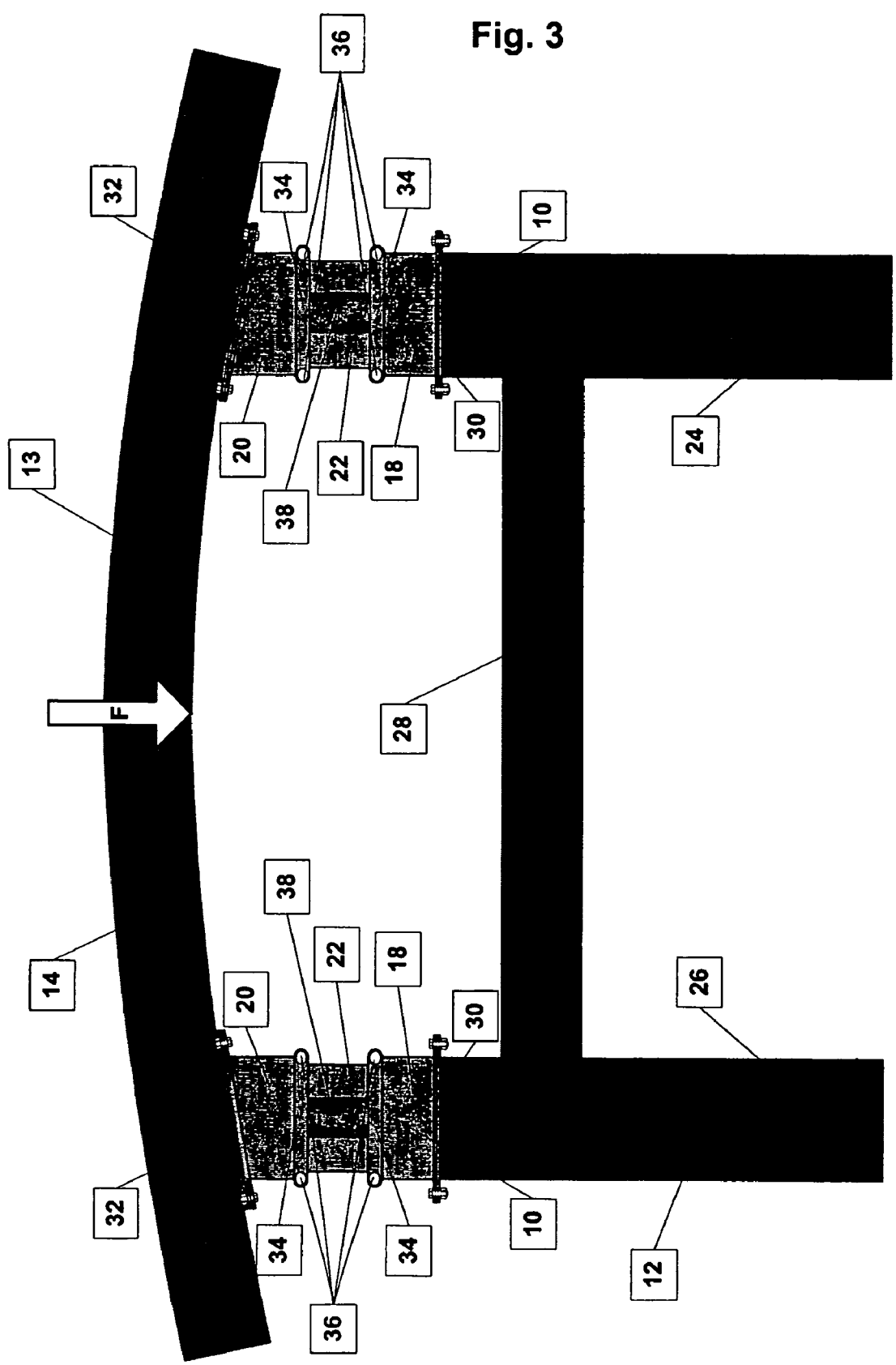
FIG. 3 is a plan view illustrating the absorbing device of FIG. 1 mounted between a frame of a motor vehicle and a bumper beam at one end of the motor vehicle.

FIGS. 1, 3 and 4 illustrate one embodiment of a collision energy-absorbing device 10 constructed according to the principles of the present invention. As illustrated in FIG. 3, a pair of collision energy-absorbing devices 10 are mounted between a frame assembly 12 and a bumper beam 14 of a motor vehicle 13 at either the front or rear end of the motor vehicle 13. The bumper beam 14 is positioned to receive collision forces and transmit the collision forces to the pair of collision energy-absorbing devices 10 during impact conditions, such as a vehicle collision. The collision energy-absorbing devices 10, as will be further discussed, collapse during the impact conditions in order to dissipate energy and thus reduce the magnitude of collision forces being transmitted to the frame assembly 12 of the motor vehicle 13.

Referring to FIGS. 3 and 4, the vehicle frame assembly 12 includes right-hand and left-hand frame rails 24, 26 that extend in the fore and aft direction of the vehicle 13. A cross-vehicle support member 28 extends transversely between the frame rails 24, 26. The cross-vehicle member 28, which can vary in length to suit various vehicle widths, is fixed directly to the frame rails 24, 26 by welding or bolting each end to the frame rails 24, 26. A support structure (not shown) for mounting the functional and decorative components associated with the front end of the motor vehicle 13 may also be mounted to the frame assembly 12. Further details of the support structure are included in U.S. Pat. No. 6,282,769, the entirety of which is incorporated by reference into the present application.

As illustrated in FIG. 1, of the collision energy-absorbing device 10 includes a substantially tubular body member 16 having a generally rectangular cross-section. The body member 16 includes opposing longitudinal end portions 18, 20 (also referred to as end shapes) and a centrally disposed intermediate portion 22 (also referred to as a medium shape) extending between the end portions 18, 20. In the illustrated embodiment, the end portions 18, 20 have a similar cross-sectional dimension. However, the end portions 18, 20 may have differing sizes that each would be larger than the intermediate portion 22. The intermediate portion 22 has a smaller cross-sectional dimension relative to the end portions 18, 20. One end portion 18, 20 is configured to be operatively connected to a forward end of the vehicle frame assembly 12 and the opposite end portion 18, 20 is configured to be operatively connected to the bumper beam 14. As shown in FIGS. 3 and 4, the end portion 18 is operatively connected to the end of the vehicle frame assembly 12 and the other end portion 20 is operatively connected to the bumper beam 14. Although the end portions 18, 20 are configured similarly, it is contemplated that the end portions 18, 20 may have different configurations which would be larger than the intermediate portion 22 to allow them to telescope over the intermediate portion 22. Also, the end portions 18, 20 could be sized to telescope within the intermediate portion 22.

Each collision energy-absorbing device 10 may be directly or indirectly fastened between the vehicle frame assembly 12 and the bumper beam 14. Each collision energy-absorbing device 10 may also be integrally formed as part of the frame assembly 12. Such integral forming may be accomplished by hydroforming the frame rails 24, 26 to provide collision energy-absorbing devices 10 as part of the frame rail's end. However, it is preferred to form the collision energy-absorbing devices 10 separately from the frame assembly 12 and the bumper beam 14 to allow for replacement of the collision energy-absorbing devices 10 after a collision. This reduces the cost of repair to the motor vehicle 13 after an accident.

As best shown in FIGS. 3 and 4, the end portion 18 of each absorbing device 10 is attached to a mounting bracket 30 to which the vehicle frame assembly 12 attaches and the opposite end portion 20 of each absorbing device 10 is attached to a mounting bracket 32 to which the bumper beam 14 attaches. The mounting brackets 30, 32 may be formed integrally with respective end portions 18, 20 of each absorbing device 10 or may be fixedly attached, by welding for example. Bolts fixedly attach the mounting bracket 30 to the vehicle frame assembly 12 and the mounting bracket 32 to the bumper beam 14. Welding may also be used for attaching the mounting brackets 30, 32 to the vehicle frame assembly 12 and bumper beam 14, respectively.

Referring to FIG. 1, each end portion 18, 20 is connected to opposite ends of the intermediate portion 22 by connecting portions 34 (also referred to as crush initiator zones). Each connecting portion 34 has a larger diametrical cross-section relative to the respective end portions 18, 20. Perforations 36 in the form of circular holes are formed in the connecting portions 34. In the illustrated embodiment, the perforations 36 are formed through corners of the connecting portions 34. However, the perforations 36 may have different configurations and may be formed through any portion of the connecting portions 34.

A protrusion 38 forms a part of the intermediate portion 22 and starts at one connection portion 34 and continues to the other connecting portion 34. In the illustrated embodiment, a pair of protrusions 38 are provided, as best shown in FIG. 4. However, it is contemplated that any number of protrusions 38 may be provided in the intermediate portion 22. The protrusions 38 shown in FIGS. 1, 3, and 4 have an arcuate cross-section, but may take on other shapes as shown in FIGS. 16–20. The protrusions 38 extend substantially along a longitudinal length of the intermediate portion 22. However, as mentioned above, the protrusions 38 may have different configurations and may be provided in one or both end portions 18, 20 and other locations as required.

The perforations 36 and protrusions 38 are provided so as to make the collapse of each collision energy-absorbing device 10 controllable, as will be further discussed.

The manner in which each collision energy-absorbing device 10 collapses is illustrated in FIGS. 5–10. FIG. 5 illustrates a section through a collision energy-absorbing device 10 in its normal, uncollapsed condition. FIG. 6 illustrates the condition of a collision energy-absorbing device 10 when a force F is initially received by the bumper beam 14 and transmitted to the ends of the frame rails 24, 26. The collision energy-absorbing device 10 begins to collapse with the end portions 18, 20 moving relatively toward one another and the connecting portion 34 starting to deform. In the next stage of collapse as illustrated in FIG. 7, the intermediate portion 22 remains intact while the end portions 18, 20 are pushed inwardly relative to the intermediate portion 22 so that the connecting portions 34 collapse and become deformed portions. The connecting portions 34 deform so that continued force allows the end portions 18, 20 to move relatively towards one another into collapsing telescoping relationship with respect to opposite ends of the intermediate portion 22. Thus, opposite ends of the intermediate portion 22 are received within the respective end portions 18, 20. FIGS. 8 and 9 illustrate the collision energy-absorbing device 10 at later stages of telescoping. A fully collapsed collision energy-absorbing device 10 is illustrated in FIG. 10.

Specifically, the connecting portions 34 that connect each end portion 18, 20 with the intermediate portion 22 are deformed beyond the elastic limit of the metal (i.e., they experience plastic deformation) allowing the end portions 18, 20 to move towards one another. These connecting portions 34 become progressively deformed as seen in FIGS. 6–9 by folding over the intermediate portion 22 into a configuration similar to that shown in FIG. 10. This folding action produces a portion 46 that extends generally parallel to the exterior surface of the intermediate portion 22 as shown in FIG. 10 allowing the end portions 18, 20 to move toward each other in a telescopic effect. The higher the amount of force F transmitted to the collision energy-absorbing device 10, the further inwardly the end portions 18, 20 will be moved toward one another and the greater the length of the deformation and the more crush is absorbed by the collision energy-absorbing device 10.

Basically, the collision energy-absorbing device 10 functions to dissipate collision energy by converting it into deformation energy as it collapses. Specifically, a portion of the collision energy is converted into the energy necessary to deform the collision energy-absorbing device 10 into its collapsed condition (as shown in FIG. 10) and thus is dissipated. As a result, the collision energy-absorbing device 10 reduces the amount of energy transmitted from the bumper beam 14 to the vehicle frame assembly 12.

Another way to describe the folding action is to say that the end portions 18, 20 are deformed into a position over top of the intermediate portion 22 that creates the folding of the connecting portions 34 back on to itself thus reducing the overall length of the device 10 in order to take up the energy. The collision energy-absorbing device 10 does not significantly expand in the horizontal or vertical direction during its collapse (i.e. its diametric dimension does not increase). The end portions 18, 20 simply move inwardly toward one another during collapsing so as to occupy a lesser volume without a significant increase in height or width.

The perforations 36 are provided in order to control or adjust the force level at which the connecting portions 34 collapse by selectively weakening the connecting portions 34. Depending on the configuration, location, and number of perforations 36, the collapse of the connecting portions 34 can be controlled to occur at a certain magnitude of force. Thus, the perforations 36 can be manipulated to control the rate of collapse.

Figure 17:
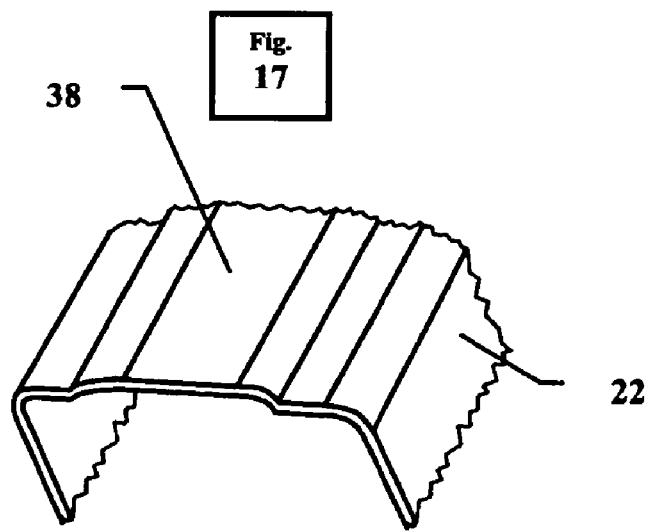
Figure 18:
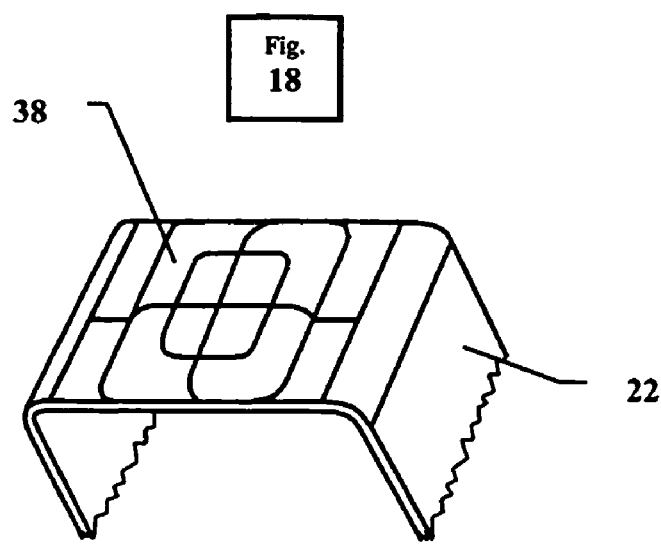
Figure 19:
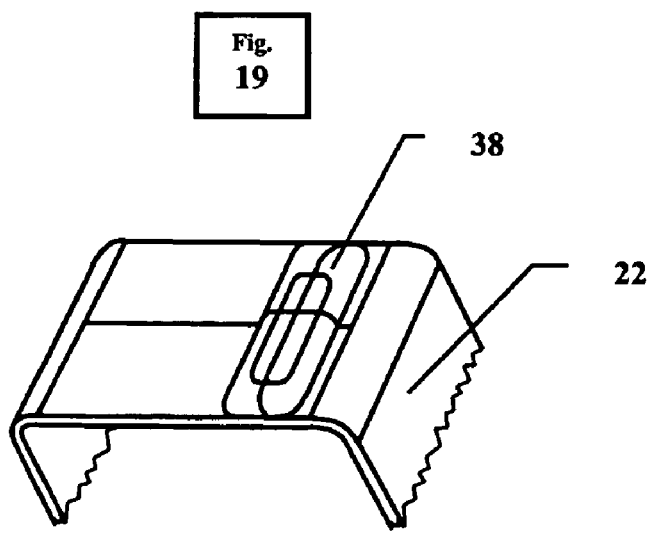
Figure 20:
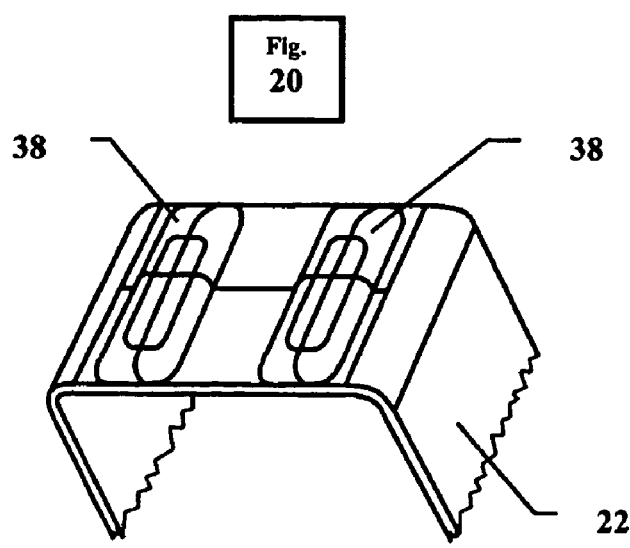

The protrusions 38 are provided to resist the telescoping movement of the end portions 18, 20 relative to the intermediate portion 22. As shown in FIGS. 16–20, the protrusions 38 may have different configurations and locations on the intermediate portion 22. The protrusions 38 may be integrally formed thereon as shown in FIG. 17 or may be formed thereon in a separate manufacturing operation as shown in FIGS. 16 and 18–20. Also, the intermediate portion 2 may have more than one protrusion 38 as shown in FIG. 20 and may be positioned on multiple sides of the intermediate portion 20 as shown in FIG. 4. As shown in FIGS. 5–10, the protrusions 38 interfere with relative movement of the connecting portions 34 and hence movement of the end portions 18, 20 in a telescopic relationship with respect to the intermediate portion 22. Specifically, as the end portions 18, 20 move relatively towards one another, the deformed connecting portions 34 engage the protrusions 38 such that the friction between the connecting portions 34 and the protrusions 38 impedes the movement of end portions 18, 20. In other words, the protrusions 38 create resistance to collapse. Depending on the configuration, location, and number of protrusions 38, the onset of telescoping can be controlled to occur at a certain magnitude of force. Thus, the protrusions 38 can be manipulated to control the rate of collapse. The protrusions 38 also add rigidity to the intermediate portion 22 or to the end portions 18, 20 to prevent buckling.

As shown in FIGS. 5–10, the connecting portions 34 fold to a position over the intermediate portion 22 as the collision energy-absorbing device 10 collapses. The protrusion 38 interferes with this relative movement by causing the connecting portions 34 to rollingly fold up and over the protrusion 38. Thus, the protrusion 38 restricts movement and increases the magnitude of force at which telescoping occurs.

Therefore, the perforations 36 and protrusions 38 add elements of control to the collision energy-absorbing device 10 to help optimize the ability of the collision energy-absorbing device 10 to control the collision energy, and hence control the rate of collapse.

Controlling the rate of collapse ensures that the collision energy-absorbing device 10 substantially dissipates collision energy and does not collapse too fast or too slow. Too fast a collapse can result in unused collision energy, which can be transferred to the vehicle frame assembly 12 and the passenger compartment. Too slow a collapse, or a substantially uncollapsed collision energy-absorbing device 10, will not dissipate collision energy and instead transfer it directly to the vehicle frame assembly 12 and to the passenger compartment.

The material thickness of the collision energy-absorbing device 10 may also be changed to control the collapse. The hydroform tooling used to make a collision energy-absorbing device 10 allows for a material thickness change at will.

There is no need to modify the frame rails 24, 26 of the vehicle frame assembly 12 in order to accommodate the collision energy-absorbing device 10. Thus, the frame rails 24, 26 of the vehicle frame assembly 12 can be made stiffer without the need for crush zones by virtue of the fact that the collision energy-absorbing devices 10 are incorporated directly into the forward end or rearward end of the vehicle frame assembly 12.

Also, because the collision energy-absorbing devices 10 collapse inwardly over themselves, they provide adequate impact crush zones without taking up a great amount of space. In other words, the diametric dimensions of the collision energy-absorbing device 10 are not significantly increased during collapse. As a result, there is little or no need to provide extra space around the periphery of the collision energy-absorbing device 10 to accommodate outward bending or buckling.

Another advantage of the manner in which the rolling folding action occurs during impact is that it provides for a relatively constant dissipation of energy over the duration of the impact. Specifically, the amount of deformation in the collision energy-absorbing device 10 is related to the magnitude of the collision forces throughout the entire collapsing. That is, the amount of deformation occurring during a collision (and hence dissipation of collision energy) is determined by the magnitude of the collision forces involved. During a collision involving relatively high collision forces, the extent to which the connecting portions 34 are deformed will be relatively higher than during collisions involving relatively low collision forces. Further, deformation can be controlled by providing the perforations 36 and protrusions 38 in the collision energy-absorbing device 10. This provides for a more effective and better-controlled energy dissipation during the vehicle collision. In comparison, members that collapse in an accordion-like manner tend to dissipate energy only during the initial stages of the collision and offer little dissipation once buckling of the accordion folds has occurred.

As aforesaid, it is preferred to form the collision energy-absorbing device 10 separately from the frame rails 24, 26 so that the collision energy-absorbing device 10 can be easily replaced after collapsing during impact. Preferably, the collision energy-absorbing devices 10 are hydroformed from a tubular metal blank. Hydroforming is a known technique that uses fluid forces to shape metal blanks. Hydroforming die assemblies performing the hydroforming technique are used for this procedure. The die assembly includes a die structure having movable upper and lower halves that cooperate to define a die cavity therebetween. The die cavity defines the desired shape of the collision energy-absorbing device 10. The tubular blank is placed in the die structure and expanded by fluid force into conformity with interior surfaces of the die structure to form the desired shape of the collision energy-absorbing device 10. Preferably, the perforations 36 in the corners of the connecting portions 34 are laser burnt after hydroforming, but drilling, piercing, or punching can also be done. Alternatively, the perforations 36 may be formed with the hydroforming die by including suitable elements for piercing. The protrusions 38 may be integrally formed by hydroforming or may be added after hydroforming. Although the illustrated collision energy-absorbing device 10 has a generally rectangular cross-section, it is contemplated that the collision energy-absorbing devices 10 may have other configurations, such as circular or other non-circular cross-sections, for example, square or polygonal.

Other methods of forming the collision energy-absorbing devices 10 are contemplated. For example, the collision energy-absorbing devices 10 may be formed integrally with the frame rails 24, 26 by hydroforming, with the bumper beam 14 being mounted on the free end of the collision energy-absorbing device 10.

The arrangement for the collision energy-absorbing device 10 is not limited to the arrangement disclosed in this application. For example, either a single collision energy-absorbing device 10 or a plurality of collision energy-absorbing devices 10 may be used to achieve the desired energy dissipation.

Further, the collision energy-absorbing devices 10 are not to be limited to a single pair of end portions 18, 20 with a single intermediate portion 22 extending therebetween. The collision energy-absorbing device 10 can take on various shapes in order to fit the required environment of the particular vehicle. Thus, a single collision energy-absorbing device 10 may have a series of wide portions and narrow portions that collapse relative to one another into a telescoping relationship.

Figure 21:
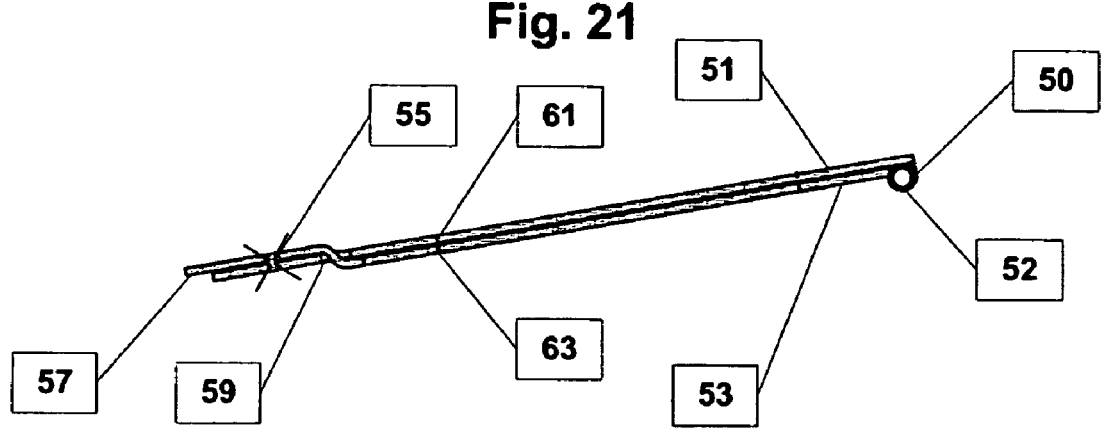
FIG. 21 is a plan view of a hinge plate assembly to be used with a collision energy-absorbing device to aid in an offset collision.
Figure 22:
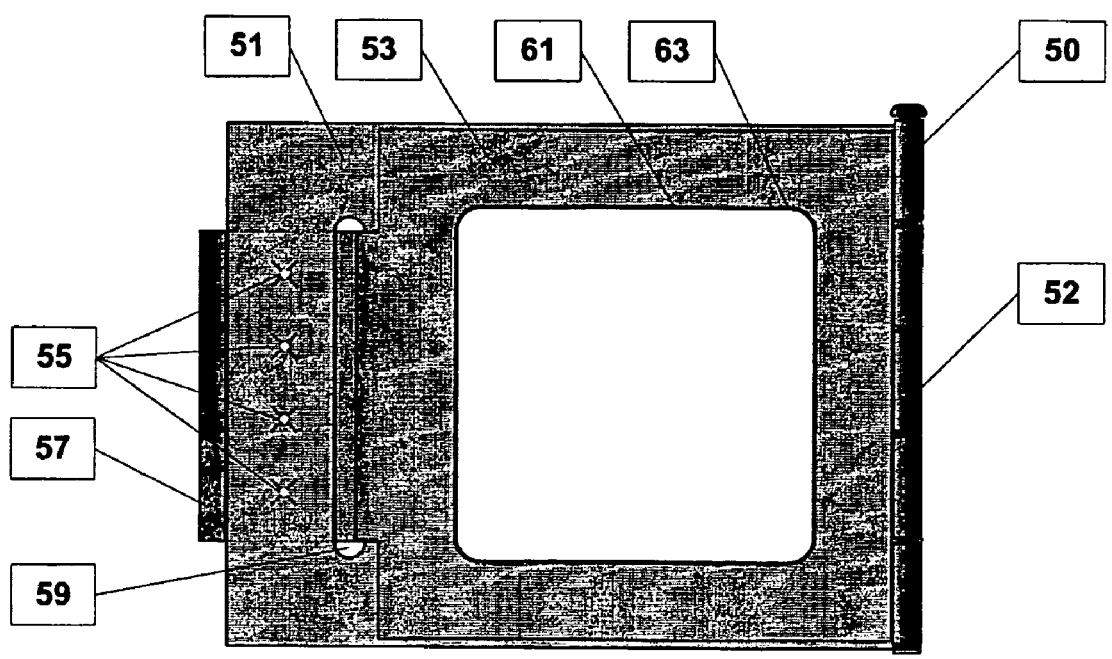
FIG. 22 is a rear view of the hinge plate assembly shown in FIG. 21.

FIGS. 21–39 illustrate a lost motion connecting structure 50 that may be installed on a collision energy-absorbing device 10 as the forward attachment to the bumper beam 14 to aid in a frontal or rear offset collision. As shown in FIGS. 21–22, the lost motion connecting structure 50 is a hinge plate assembly that includes a first mounting plate 51 and a second mounting plate 53 pivotally connected by a hinge 52. The hinge plate assembly 50 is movable from a closed position in which the first and second plate members 51, 53 are positioned adjacent one another (FIGS. 21 and 22) to an open position in which the second mounting plate 53 is pivoted relative to the first mounting plate 51, as will be further discussed. The second mounting plate 53 includes a bent tab portion 57 that extends through a slot 59 provided in the first mounting plate 51. A series of welds 55 are provided to secure the bent tab portion 57 to the first mounting plate 51. In the illustrated embodiment, four welds 55 are provided. However, it is contemplated that any number of welds may be provided depending on vehicle requirements, as will be discussed below. Further, the first and second mounting plates 51, 53 include aligned openings 61, 63, respectively, therethrough to reduce the weight of the assembly.

In an offset collision, the hinge plate assembly 50 permits the side of the bumper beam 14 opposite the impact to move relative to the collision energy-absorbing device thereof. Thus, the vehicle will not move with the bumper beam and the collision energy-absorbing device 10 on the side of the impact will absorb a substantial portion of the load, as will be further discussed. (See FIGS. 32–39)

Figure 23:
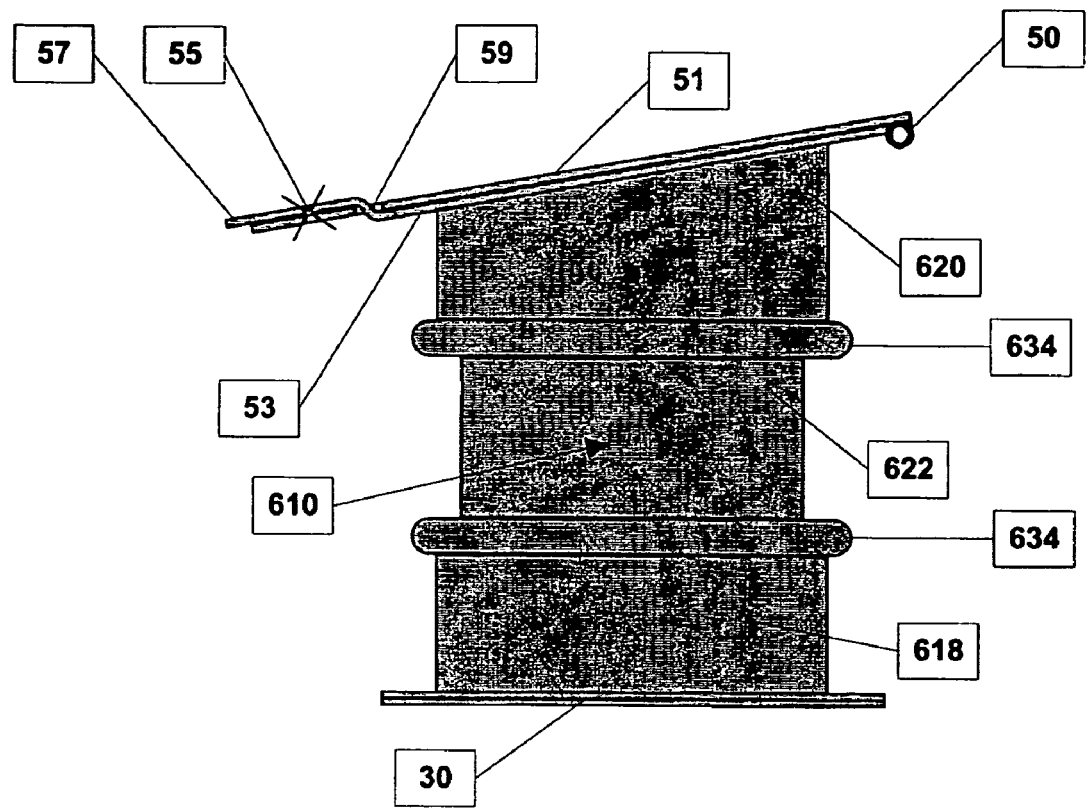
FIG. 23 is a plan view of an assembled replaceable hinge plate assembly and collision energy-absorbing device to aid in an offset collision.
Figure 24:
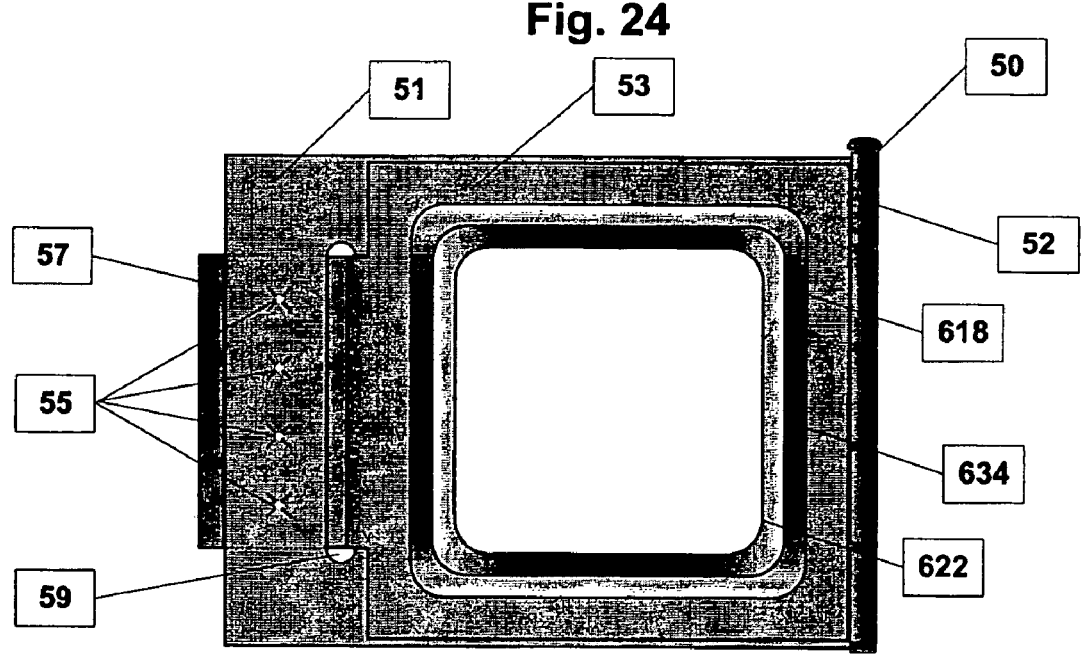
FIG. 24 is a rear view of the assembled replaceable hinge plate assembly and collision energy-absorbing device shown in FIG. 23.
Figure 25:
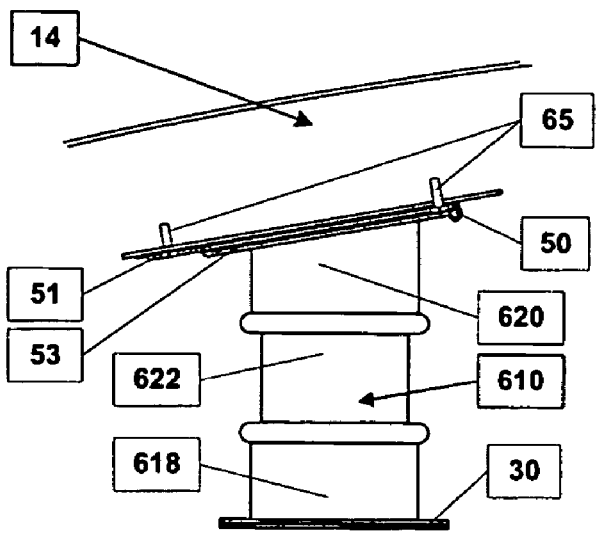
FIG. 25 is a cross-sectional view of an energy-absorbing system used in an offset collision.
Figure 26:
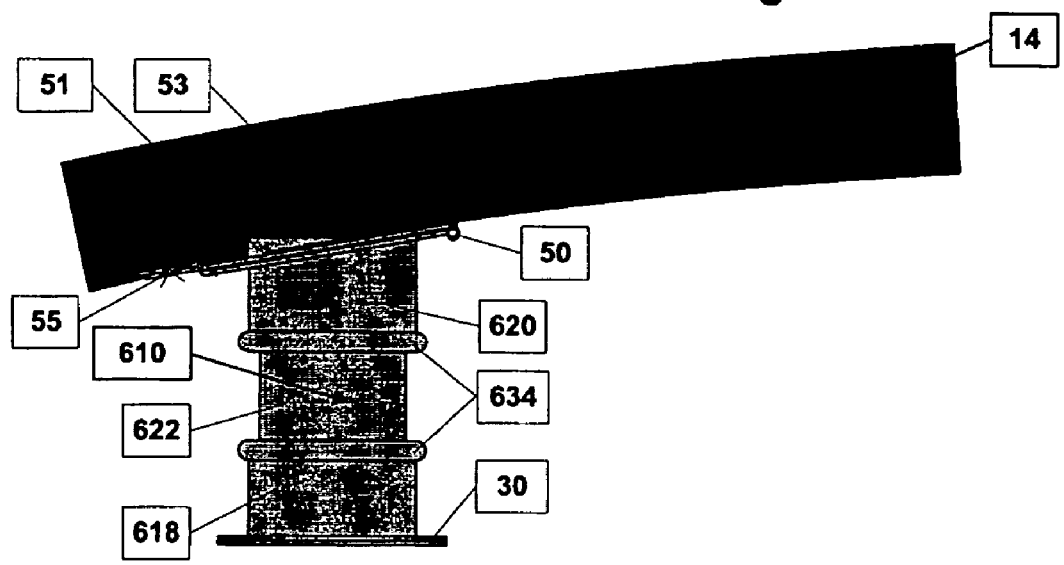
FIG. 26 is a plan view of an energy-absorbing system used in an offset collision.

FIGS. 23–24 illustrate the combination of the hinge plate assembly 50 and a collision energy-absorbing device 610. The collision energy-absorbing device 610 illustrated in FIGS. 23–39 includes opposite end portions 618, 620 and intermediate portion 618. The device 610 illustrated includes no protrusions and perforations. However, the device may include any number and configuration of protrusions and perforations. As illustrated, a hinge plate assembly 50 is connected to the end portion 620 of the collision energy-absorbing device 610 and a mounting plate 30 is connected to the opposite end portion 618. As illustrated, the end portion 620 is connected to the second mounting plate 53 of the hinge plate assembly 50.

Figure 27:
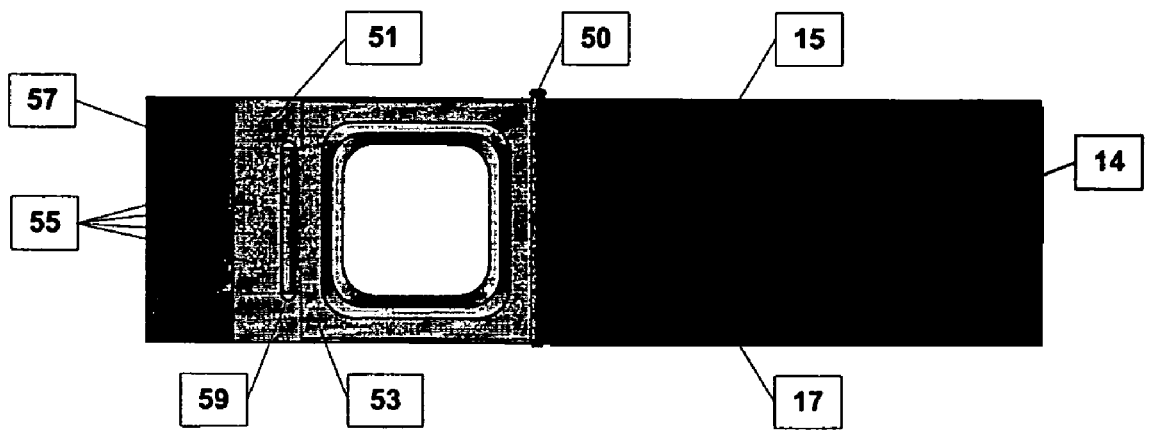
FIG. 27 is a rear view of the energy-absorbing system shown in FIG. 26.
Figure 28:
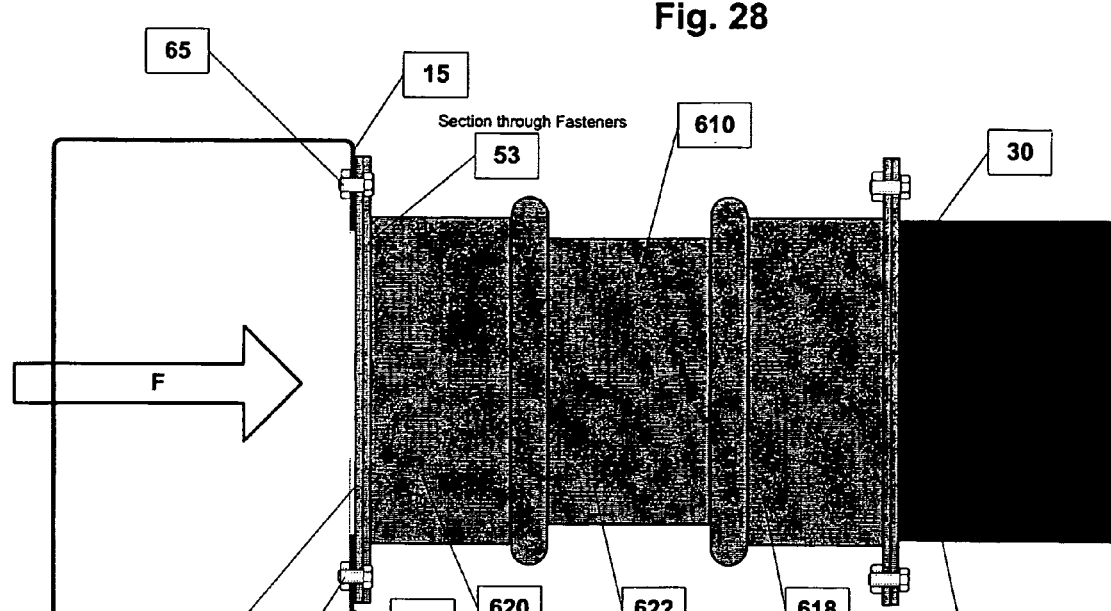
FIG. 28 is a cross-sectional view of an energy-absorbing system used in an offset collision.
Figure 29:
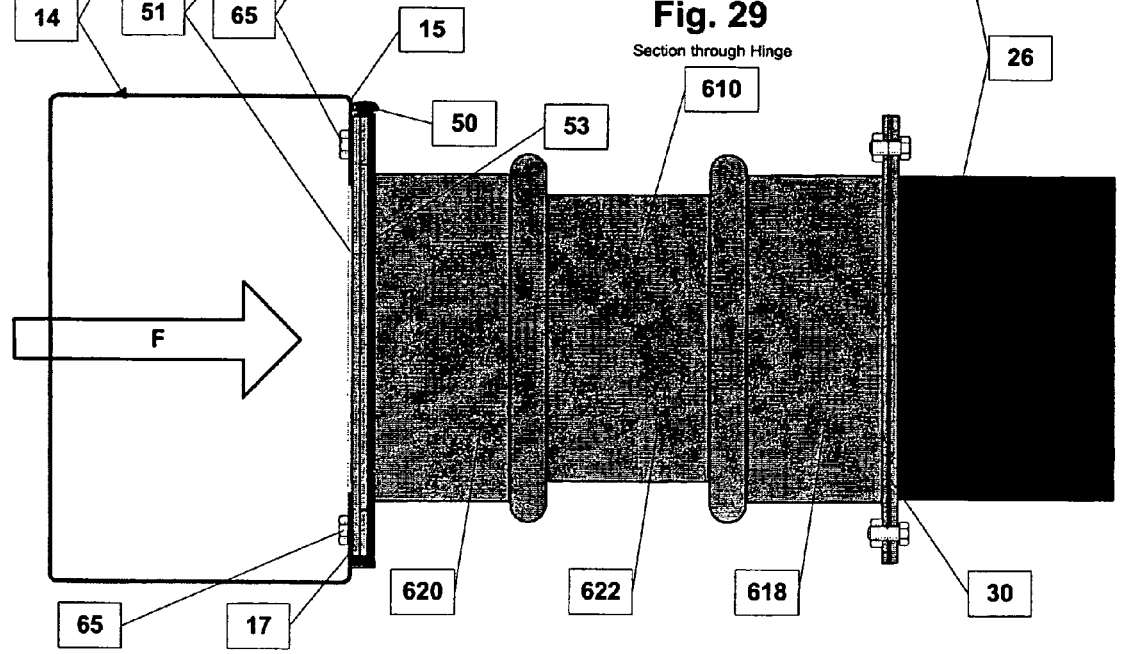
FIG. 29 is another cross-sectional view of an energy-absorbing system used in an offset collision.

FIGS. 25–29 show the end portion 620 with the hinge plate assembly 50 attached thereto connected to the bumper beam 14. As illustrated, the first mounting plate 51 of the hinge plate assembly 50 is connected to the bumper beam 14. Specifically, the bumper beam 14 includes a pair of flanges 15, 17 that extend inwardly towards one another, as shown in FIG. 27–29. As most clearly illustrated in FIG. 28 and 29, upper and lower ends of the first mounting plate 51 are secured to the flanges 15, 17 by fasteners 65. The fasteners are not illustrated in FIGS. 26, 27, and 30–39. The first mounting plate 51 may also be secured to flanges 15, 17 of the bumper beam 14 by welding.

Figures 30, 31:
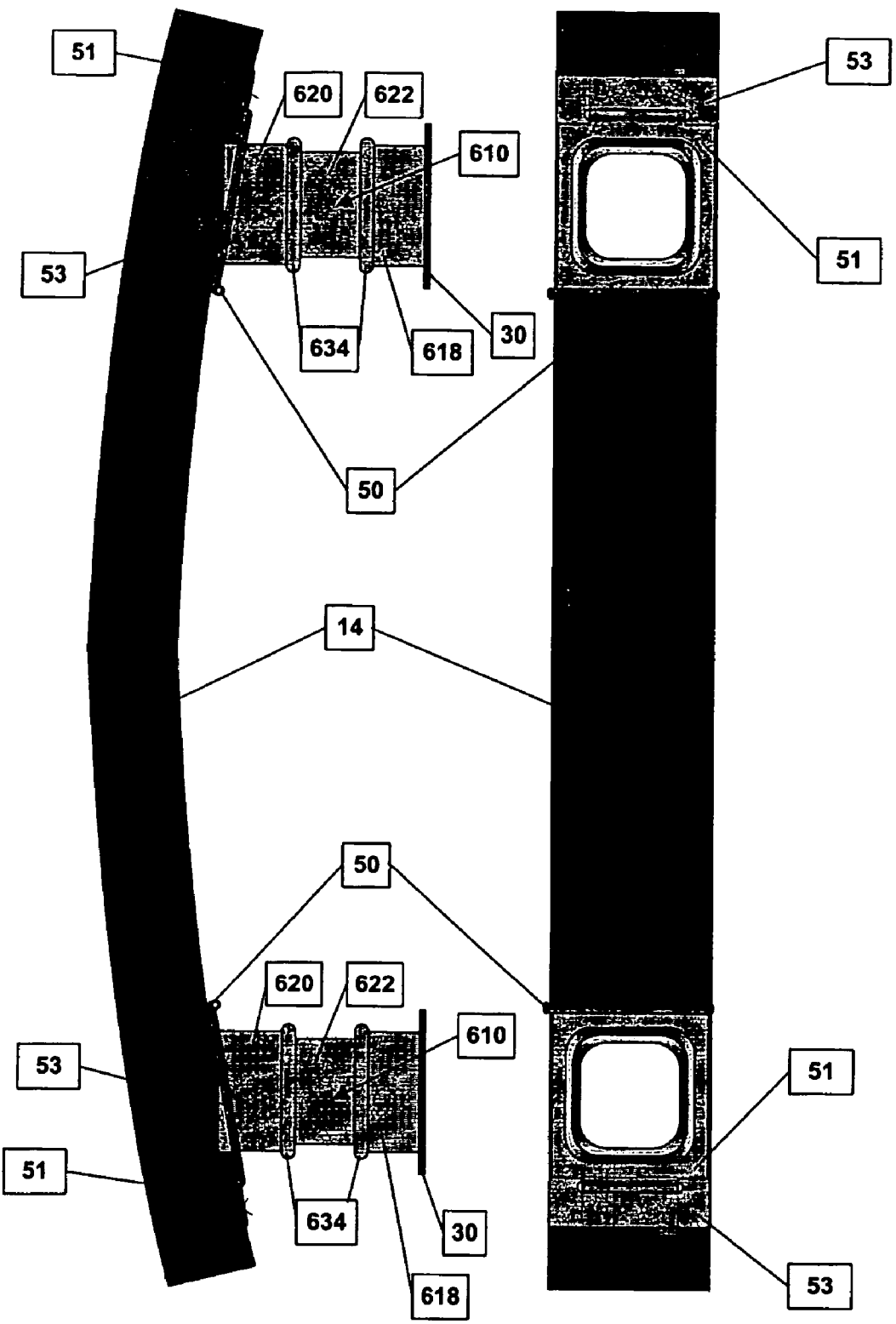
FIG. 30 is a plan view of a complete hinged energy-absorbing system used in an offset collision.
FIG. 31 is a rear view of the complete hinged energy-absorbing system shown in FIG. 30.

FIGS. 30–31 show the bumper beam 14 with a pair of collision energy-absorbing devices 610 each with hinge plate assemblies 50 attached at the bumper beam 14 and each with mounting plates 30 to which respective frame rails 24, 26 would be mounted.

FIGS. 32–33 show the initial stages of an offset collision. As illustrated, in an offset collision, the impact occurs at one end of the bumper beam 14. With a rigid, non-hinged connection, during impact, the opposite end of the bumper beam pivots and tends to pivot the vehicle due to the rigid connection with the vehicle frame assembly. Specifically, as the end of the bumper beam 14 which has been impacted is forced in towards the frame assembly, the opposite end swings in a direction away from the frame assembly. This tends to pull on that side of the frame assembly and pivot the vehicle in a yaw-type movement. When the hinge plate assembly 50 is incorporated into each of the collision energy-absorbing devices 610, the hinge plate assembly 50 opposite the impact point moves to an open position during the frontal offset collision which reduces the amount of or eliminates pivotal movement of the vehicle about the point of impact. As shown in FIG. 32, the first plate member 51 pivots relative to the second plate member 53 as the hinge plate assembly 50 moves to the open position. Specifically, during impact, as the opposite end of the bumper beam 14 pivots, the first plate member 51 pivots along with the bumper beam 14 relative the second plate member 53 fixed to the collision energy-absorbing device. Thus, the bumper beam 14 pivots relative to the collision energy-absorbing device and hence the vehicle frame assembly resulting in "lost motion". In other words, the pivoting movement of the bumper beam 14 will not significantly transfer to the collision energy absorbing device and hence to the vehicle frame assembly. Thus, the pivotal movement of the vehicle with the bumper beam is substantially reduced and the impact is substantially absorbed by the collision energy absorbing device 10 on the side of the impact with the hinge plate assembly 50 thereof remaining in a closed position. Further, the pair of hinge plate assemblies illustrated in FIG. 32 are configured and positioned such that only one of the pair of hinge plate assemblies can move to an open position at a time during an offset collision.

FIGS. 34–39 illustrate the manner in which the hinge plate assembly pivots from a closed position to an open position during an offset collision. FIG. 34 illustrates the relation between the first and second plate members when a force F is initially received by the bumper beam 14. As the opposite end of the bumper beam 14 pivots, the first plate member 51 pivots along with the bumper beam 14 relative the second plate member 53 fixed to the collision energy-absorbing device. As the first plate member 51 pivots, the series of welds 55 that secure the bent tab portion 57 to the first mounting plate 51 fail such that the bent tab portion 57 begins to move relative to the first plate member. Specifically, the first plate member 51 continues to move relative to the first plate member which deforms the bent tab portion 57 positioned through the slot 59 thereof. In the next stage of collapse as illustrated in FIG. 36, the bent tab portion 57 is further deformed by the first mounting plate 51 as the first mounting plate 51 continues to pivot with the bumper beam 14. The bent tab portion 57 deforms so that continued force allows the plate members 51, 53 to pivot relative to one another about the hinge 52. FIG. 38 illustrates the hinge plate assembly 50 in a substantially open position. As illustrated, the bent tab portion 57 has been deformed such that it extends generally perpendicular with respect to the first mounting structure 51 and the frame 14 thereof The configuration of the welds 55 may be controlled such that the welds 55 fail at different magnitudes of force depending on the requirements of the vehicle.

It is contemplated that the lost motion connecting structure 50 may be a sliding mechanism wherein a first portion thereof is mounted to the bumper beam and a second portion thereof is mounted to the collision energy absorbing device with the first and second portions slidably mounted to one another for movement relative to one another. The lost motion connecting structure 50 may also be an accordion-type structure that would allow relative movement between the bumper beam and the collision energy-absorbing device.

FIGS. 2, 11–14, and 40–47 illustrate alternative embodiments of the collision energy-absorbing device 10. Elements in the alternative embodiments of the collision energy-absorbing device 10 that are similar to elements of the collision energy-absorbing device 10 have corresponding reference numerals.

FIG. 2 illustrates a collision energy-absorbing device 110 having end portions 118, 120 and an intermediate portion 122 therebetween. Connecting these portions are two connection portions 134. Each portion 118, 120, 122 has a different cross-section relative to one another with the end portion 120 having the smallest cross-section and the end portion 118 having the largest cross-section. As the collision energy-absorbing device 110 collapses during an impact condition, the end portion 120 and intermediate portion 122 move in telescoping relation with the end portion 120 being received within the intermediate portion 122. The intermediate portion 122 and the end portion 118 also move in telescoping relation with the intermediate portion 122 being received within the end portion 118. The collision energy-absorbing device 110 includes perforations 136 and protrusions 138 to control the rate of collapse.

Figure 13:
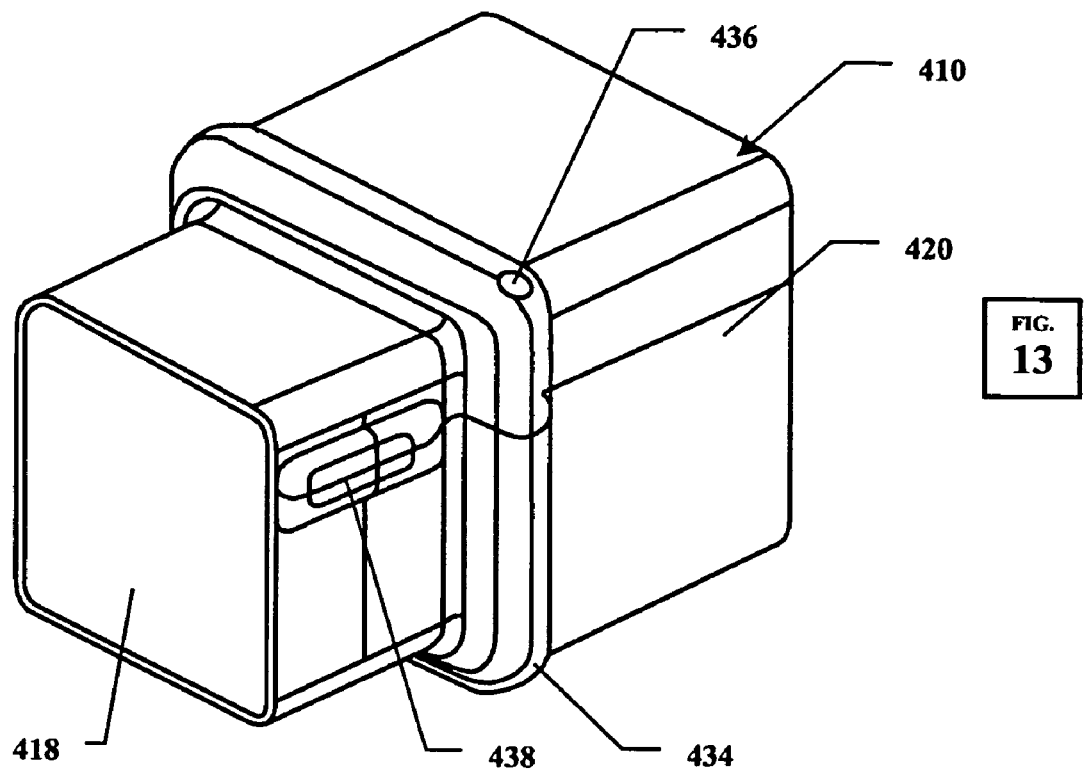
Figure 14:
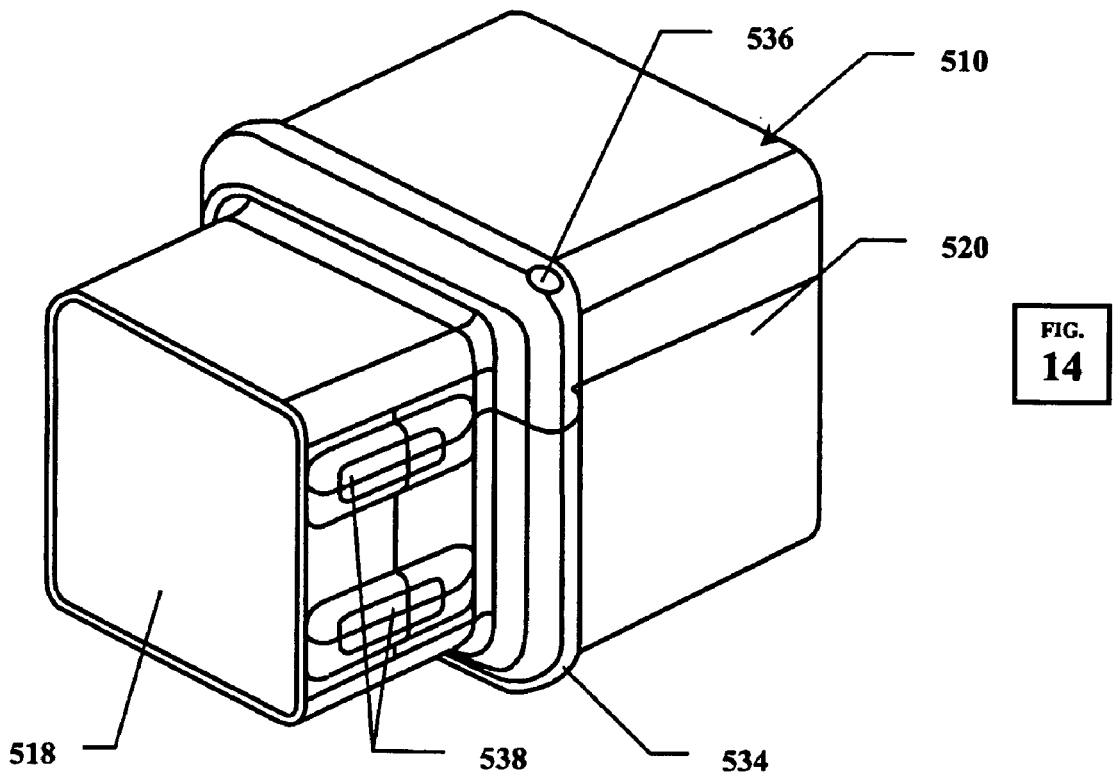
Figure 15:
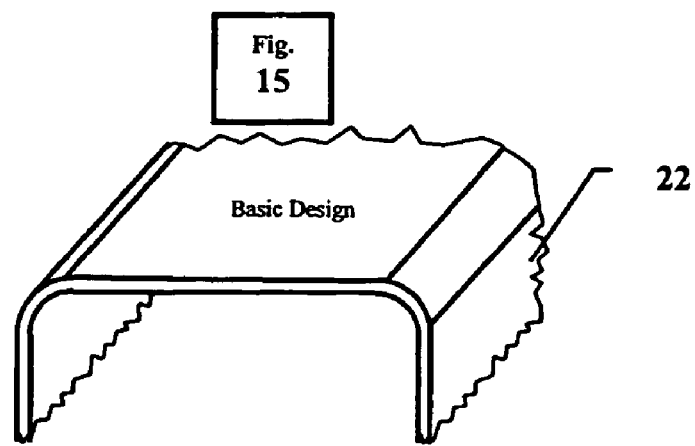
FIGS. 15–20 are cross-sectional views illustrating different embodiments of the intermediate portions of the collision energy-absorbing device shown in FIG. 1.
Figure 16:
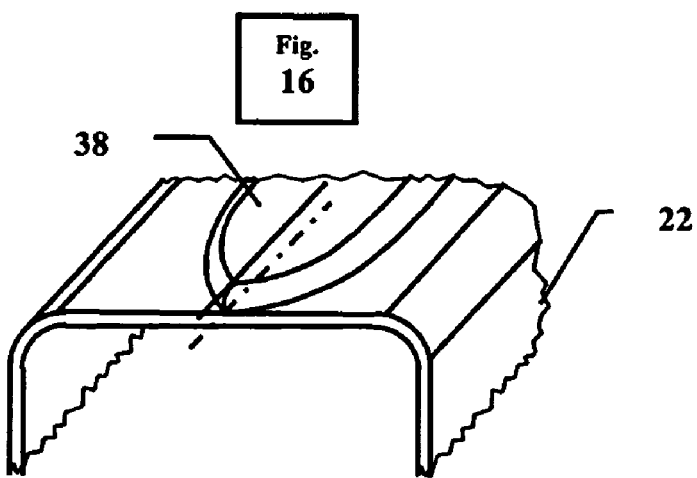

FIGS. 11–14 illustrate different embodiments of collision energy-absorbing devices 210, 310, 410, 510 having opposing end portions of different cross-sectional dimensions interconnected by a connecting portion 234, 334, 434, 534. As the collision energy-absorbing device 210, 310, 410, 510 collapses during an impact condition, the end portions move in telescoping relation with a deformed portion being received between the end portions. The collision energy-absorbing devices 210, 310, 410, 510 include perforations 236, 336, 436, 536 and protrusions 238, 338, 438, 538 to control the rate of collapse. As illustrated, the protrusions 238, 338, 438, 538 in each of FIGS. 11–14 have different configurations and locations. For example, the device 510 includes a pair of spaced apart protrusions 538 as shown in FIG. 14 and the device 410 includes a single offset protrusion 538 as shown in FIG. 13.

FIGS. 40–41 illustrate a collision energy-absorbing device 710 similar in configuration to the collision energy-absorbing device 10 shown in FIG. 1. In contrast to the collision energy-absorbing device 10 in FIG. 1, this collision energy-absorbing device 710 has a circular cross-section, as shown in FIG. 41. The collision energy-absorbing device 710 includes perforations 736 in one of the connecting portions 734 and protrusions 738 in the intermediate portion 722 to control the rate of collapse.

FIGS. 42–43 illustrate a collision energy-absorbing device 810 having opposing end portions 818, 820 and a pair of intermediate portions 822, 823 therebetween. The connecting portions 834 interconnect adjacent portions with one another. The end portion 820 is configured such that it may be positioned inside the bumper beam 14 and attached directly to it without the use of a mounting bracket. As the collision energy-absorbing device 810 collapses during an impact condition, the end portion 818 and the intermediate portion 823 move in telescoping relation with opposing ends of the other intermediate portion 822 being received inside the intermediate portion 823 and the end portion 818 attached to the frame rail. The intermediate portion 823 and the end portion 820 attached to the bumper beam 14 move in a telescoping relationship with the end portion 820 being received within the intermediate portion 823. The collision energy-absorbing device 810 includes perforations 836 in each of the connecting portions 834 and protrusions 838 in the end portion 820 and the intermediate portion 822 to control the rate of collapse. The protrusions 838 in the end portion 820 are in the form of a pair of spaced apart protrusions 838*a*, 838*b*.

Figure 45:
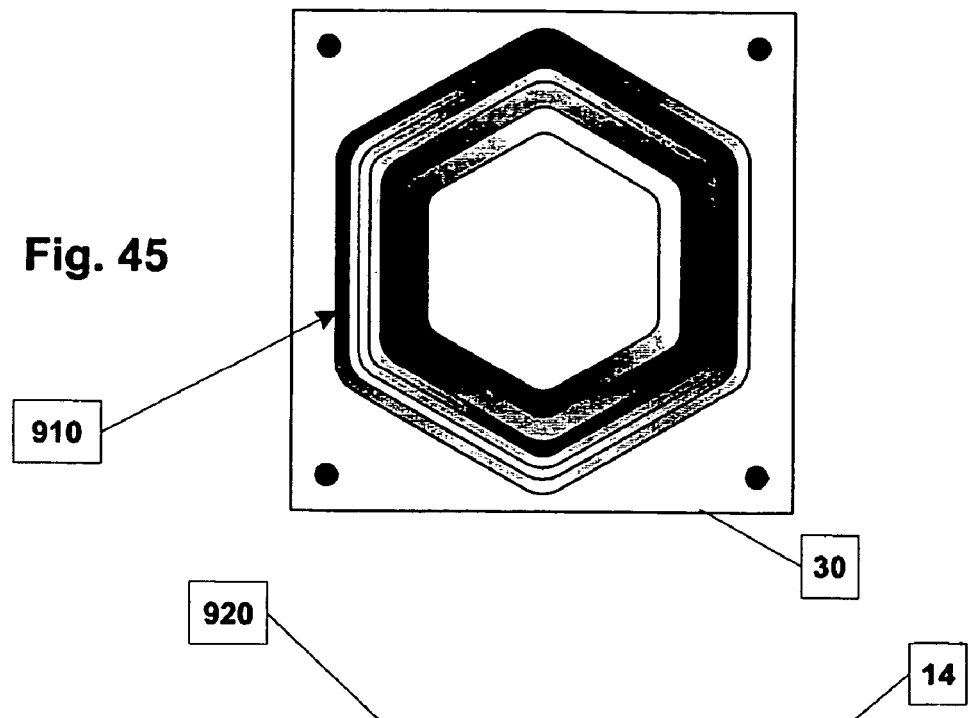
FIG. 45 is a rear view of the collision energy-absorbing device shown in FIG. 44.
Figure 44:
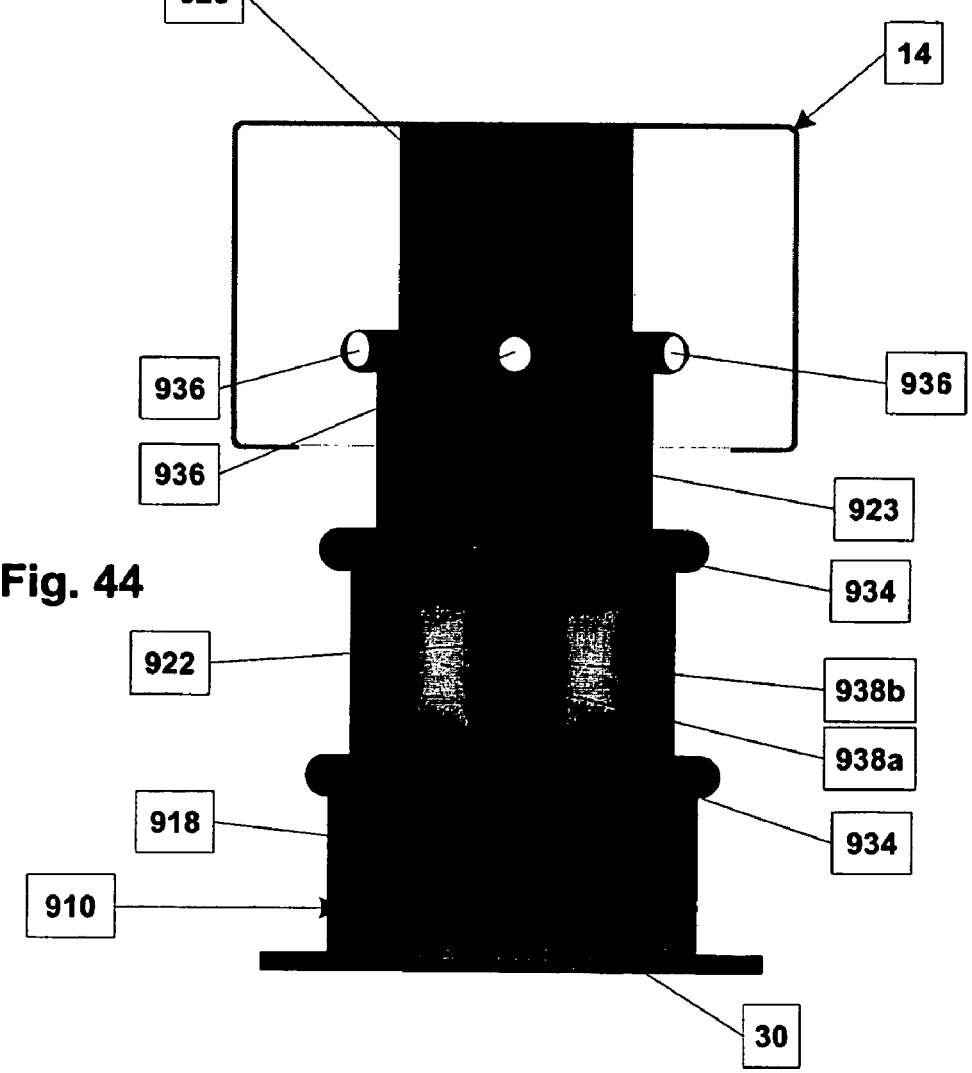
FIG. 44 is a plan view of an octagon collision energy-absorbing device having a 3-stage design with protrusions and perforations and being attached to the bumper face that allows absorption during the initial vehicle impact.

FIGS. 44–45 illustrate a collision energy-absorbing device 910 having opposing end portions 918, 920 and a pair of intermediate portions 922, 923 therebetween. The collision energy-absorbing device 910 has a generally hexagonal cross-section, as shown in FIG. 45. The connecting portions 934 interconnect adjacent portions with one another. The end portion 920 is configured such that it may be positioned inside the bumper beam 14 and attached to its face without the use of a mounting bracket. Each portion 918, 929, 922, 923 has a different cross-section relative to one another. The end portion 920 has the smallest cross-section and the end portion 918 has the largest cross-section with the cross-sections of the intermediate portions 923, 922 respectively increasing therebetween. As the collision energy-absorbing device 910 collapses during an impact condition, the end portion 920 and the intermediate portion 923 move in telescoping relation with the end portion 920 being received within the intermediate portion 923. The intermediate portion 923 and the intermediate portion 922 also move in telescoping relation with the intermediate portion 923 being received within the intermediate portion 922. The end portion 918 and the intermediate portion 922 also move in telescoping relation with the intermediate portion 922 being received within the end portion 918. The collision energy-absorbing device 910 includes perforations 936 in the connecting portions 934 and protrusions 938 in the form of a pair of spaced apart protrusions 938*a*, 938*b* in the intermediate portion 922, to control the rate of collapse.

Figure 47:
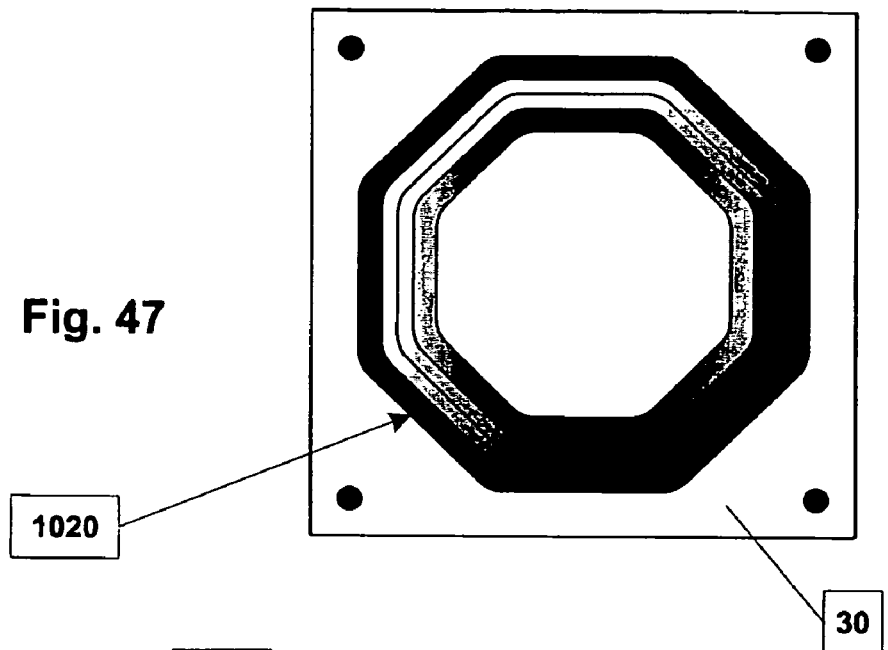
FIG. 47 is a rear view of the collision energy-absorbing device shown in FIG. 46.
Figure 46:
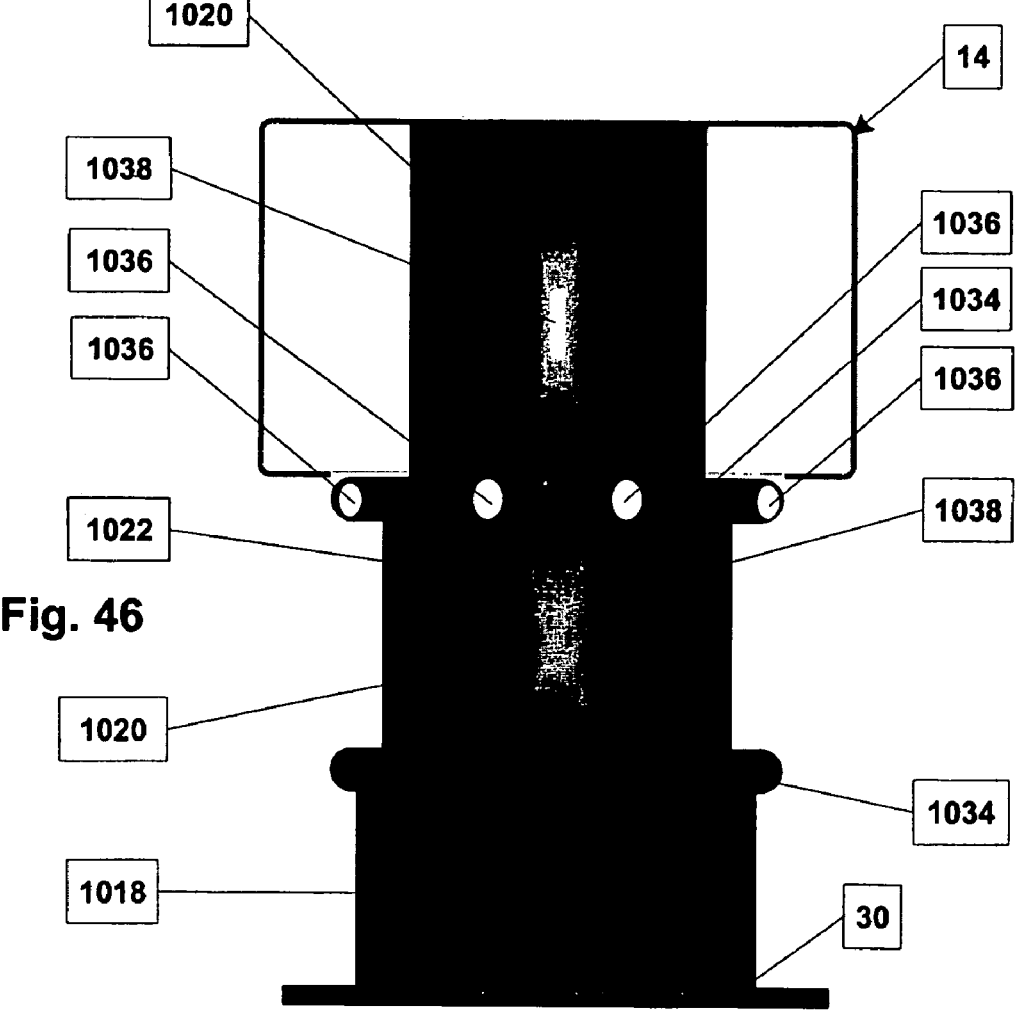
FIG. 46 is a plan view of a hexagon collision energy-absorbing device having a 2-stage design with protrusions and perforations and being attached to the bumper face that allows absorption during the initial vehicle impact.

FIGS. 46–47 illustrate a collision energy-absorbing device 1010 similar in configuration to the collision energy-absorbing device 110 in FIG. 2. In contrast to the collision energy-absorbing device 110 in FIG. 2, the collision energy-absorbing device 1010 has an octagonal cross-section, as shown in FIG. 47. The collision energy-absorbing device 1010 also includes perforations 1036 in one of the connecting portions 1034 and protrusions 1038 in the intermediate portion 1022 and the end portion 1018 to control the rate of collapse. In the illustrated embodiment, the perforations 1036 are formed through an intermediate portion of one of the connecting portions 1034 as well as through the corners.

It should be noted that the plurality of embodiments of the collision energy-absorbing device described above may be combined in any way so as to fit the required environment of the particular vehicle.

The collision energy-absorbing devices of the present invention may be included in any type of vehicle, including space framed vehicle, unibody vehicles, conventionally framed vehicles, and modular vehicle assemblies.

For the purposes of the present application, the bumper beam and the collision energy-absorbing device may be considered together as an energy-absorbing system that absorbs and dissipates collision energy that would otherwise be transmitted to a space framed vehicle, unibody vehicle, conventionally framed vehicle, or a modular vehicle assembly.

As described above, the collision energy absorbing device can have an infinite number of configurations by modifying the cross-sectional configuration, the configuration of the perforations and protrusions, and the number and configuration of portions that are interconnected with one another. The configuration of the collision energy-absorbing device largely depends on the specific design of the vehicle.

It can thus be appreciated that the objectives of the present invention have been fully and effectively accomplished by the foregoing preferred embodiments. It should be understood, however, that these embodiments have been provided to illustrate the structural and functional principles of the present invention and are not intended to be limiting. To the contrary, the present invention is intended to encompass all modifications, alterations, and substitutions within the scope of the appended claims.

What is claimed:

1. A collision energy-absorbing device for mounting between a frame assembly of a motor vehicle and a bumper beam at one end of the motor vehicle, said collision energy-absorbing device comprising:

a substantially tubular body member configured to be operatively connected between the vehicle frame assembly and the bumper beam, said body member being constructed and arranged to collapse as said bumper beam and said vehicle frame assembly are moved relatively toward one another during a vehicle collision, said body member having a substantially tubular first telescoping portion and a substantially tubular second telescoping portion, said first and second telescoping portions being connected by a connecting portion, said first and second telescoping portions having different cross-sectional dimensions configured to enable said first and second telescoping portions to move one within the other into collapsing telescoping relation as said body member collapses with said connecting portion being deformed and received between said first and second telescoping portions, said body member further including one or more protrusions extending from one of said first and second telescoping portions, said protrusions being configured to interfere with relative movement of the other of said first and second telescoping portions as said body member collapses to thereby retard movement of said first and second telescoping portions one within the other into said telescoping relation; and a lost motion connecting structure carried on the body member for connection to the bumper beam, the lost motion connecting structure configured and positioned to allow the bumper beam to move relatively away from the body member during an offset collision laterally opposite the device, wherein the lost motion connecting structure includes a hinge plate assembly having a first mounting plate and a second mounting plate pivotally connected by a hinge, one of the first and second mounting plates being connected to the body member and the other of the first and second mounting plates being connected to the bumper beam, wherein the hinge plate assembly is movable from a closed position in which the first and second mounting plates are adjacent one another to an open position in which the first and second mounting plates are pivoted relative to one another during the offset collision.

* * * * *